(12) United States Patent
Stokes et al.

(10) Patent No.: US 10,675,031 B2
(45) Date of Patent: Jun. 9, 2020

(54) CLIP RETENTION FOR SURGICAL CLIP APPLIER

(71) Applicant: Ethicon LLC, Guaynabo, PR (US)

(72) Inventors: Michael J. Stokes, Cincinnati, OH (US); Gregory G. Scott, Cincinnati, OH (US); Michael A. Murray, Bellevue, KY (US); Ryan J. Laurent, Loveland, OH (US); Disha V. Labhasetwar, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 253 days.

(21) Appl. No.: 15/674,075

(22) Filed: Aug. 10, 2017

(65) Prior Publication Data

US 2019/0046197 A1 Feb. 14, 2019

(51) Int. Cl.
| | | |
|---|---|---|
| *A61B 17/10* | (2006.01) | |
| *A61B 17/128* | (2006.01) | |
| *A61L 31/06* | (2006.01) | |
| *A61L 31/14* | (2006.01) | |
| *A61B 17/00* | (2006.01) | |

(52) U.S. Cl.
CPC ........ *A61B 17/105* (2013.01); *A61B 17/1285* (2013.01); *A61L 31/06* (2013.01); *A61L 31/14* (2013.01); *A61B 2017/00367* (2013.01); *A61B 2017/00831* (2013.01); *A61B 2017/00862* (2013.01); *A61B 2017/00884* (2013.01); *A61L 2400/16* (2013.01)

(58) Field of Classification Search
CPC ............. A61B 17/105; A61B 17/1285; A61B 2017/00367; A61B 2017/00831; A61B 2017/00862; A61B 2017/00884; A61L 31/06; A61L 31/14; A61L 2400/16
See application file for complete search history.

(56) References Cited

U.S. PATENT DOCUMENTS

| | | |
|---|---|---|
| 4,979,950 A | 12/1990 | Transue et al. |
| 6,824,547 B2 | 11/2004 | Wilson, Jr. et al. |
| 2010/0274262 A1* | 10/2010 | Schulz ............... A61B 17/1285 606/142 |
| 2015/0080879 A1 | 3/2015 | Trees et al. |
| 2019/0046198 A1 | 2/2019 | Stokes et al. |

* cited by examiner

*Primary Examiner* — George J Ulsh
(74) *Attorney, Agent, or Firm* — Mintz Levin Cohn Ferris Glovsky and Popeo, P.C.

(57) ABSTRACT

A surgical clip applier is provided that includes first and second jaws on a distal end of an elongate shaft, a clip advancing assembly extending through the shaft and configured to advance a distal-most clip from a plurality of clips in the shaft into the first and second jaws. The jaws have opposed inward facing surfaces, and each inward facing surface has a clip track defined therein for receiving and guiding legs of a clip into the first and second jaws. The clip track of at least one of the jaws has at least one deflectable clip retention member disposed therein and configured to apply a biasing force to a leg of a clip disposed within the jaws to thereby retain the clip within the jaws and maintain alignment of the clip with respect to the jaws. The clip track of at least one of the jaws may also have at least one recess or protrusion designed to be complementary to and mate with a protrusion or recess in a clip.

19 Claims, 29 Drawing Sheets

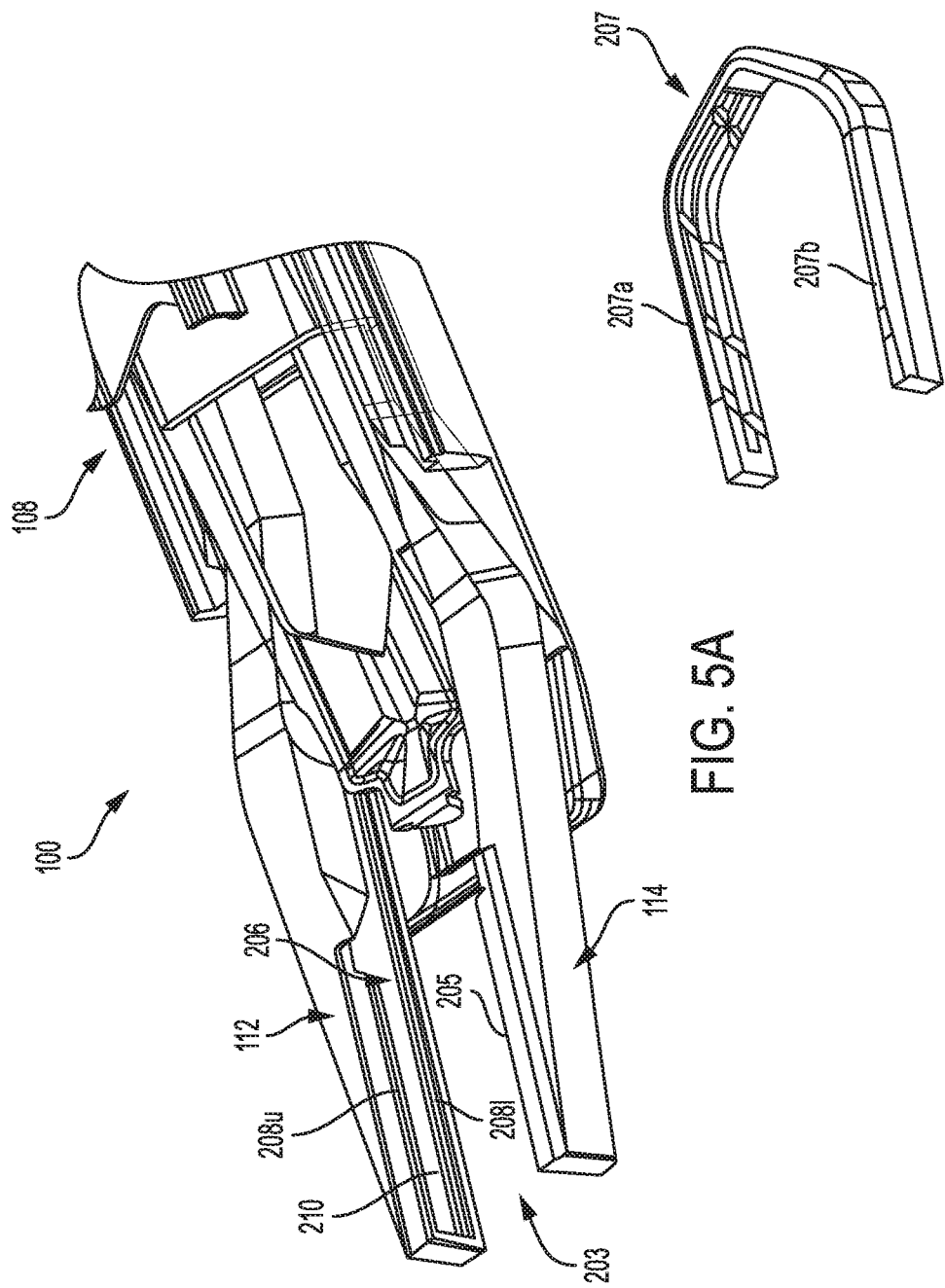

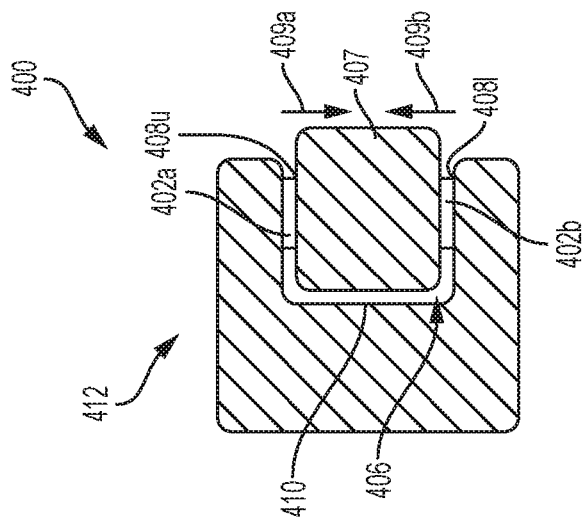
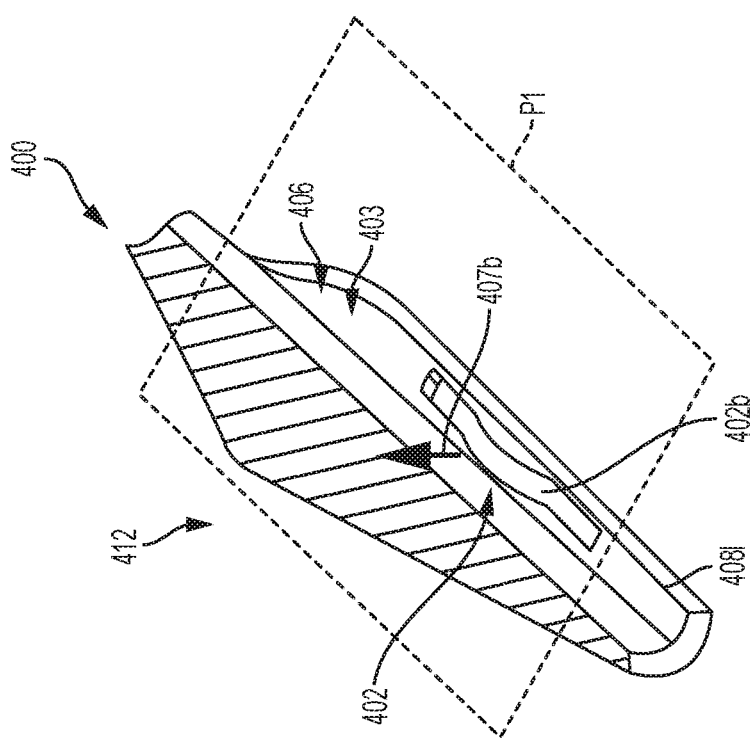
FIG. 9B
FIG. 9A

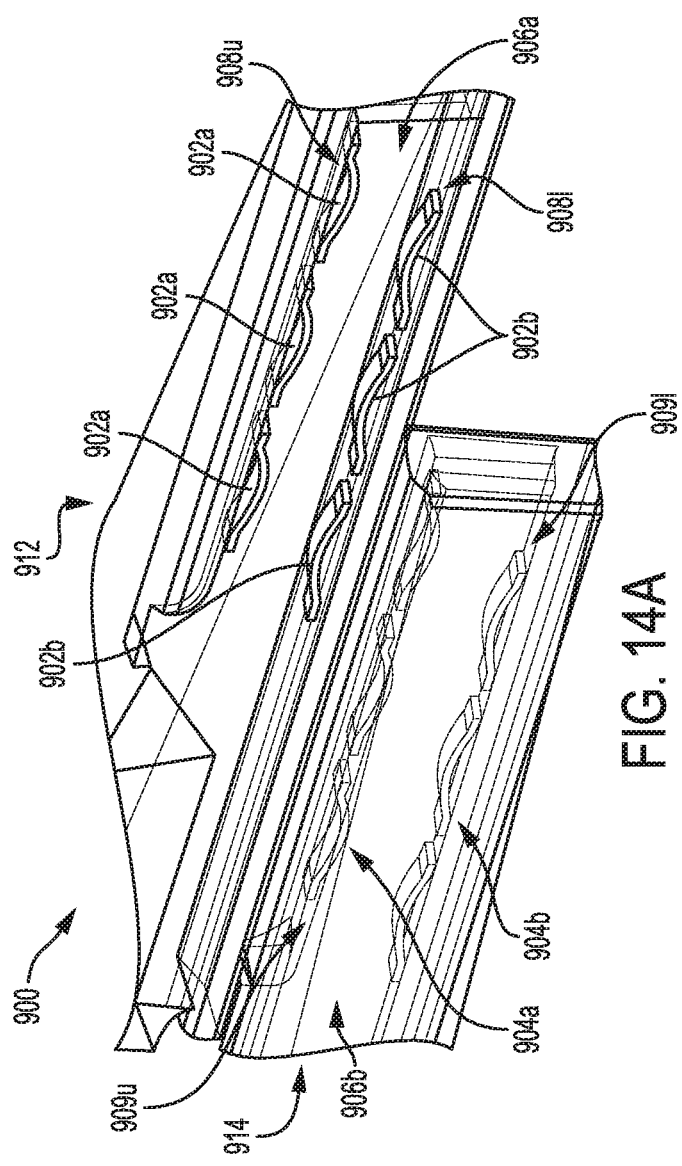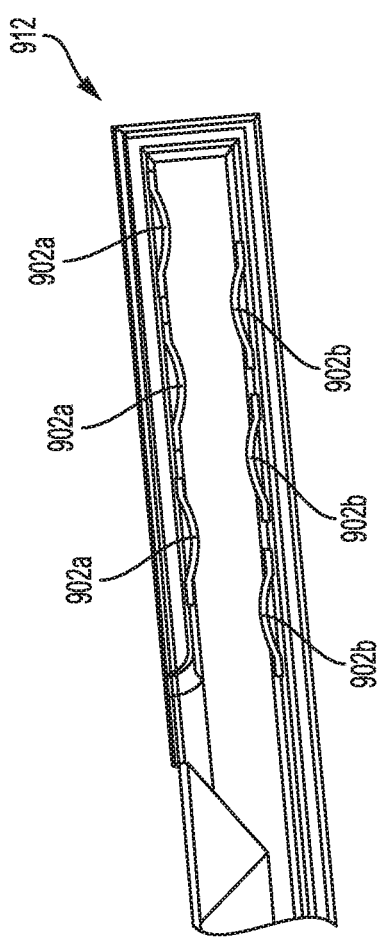
FIG. 14A
FIG. 14B

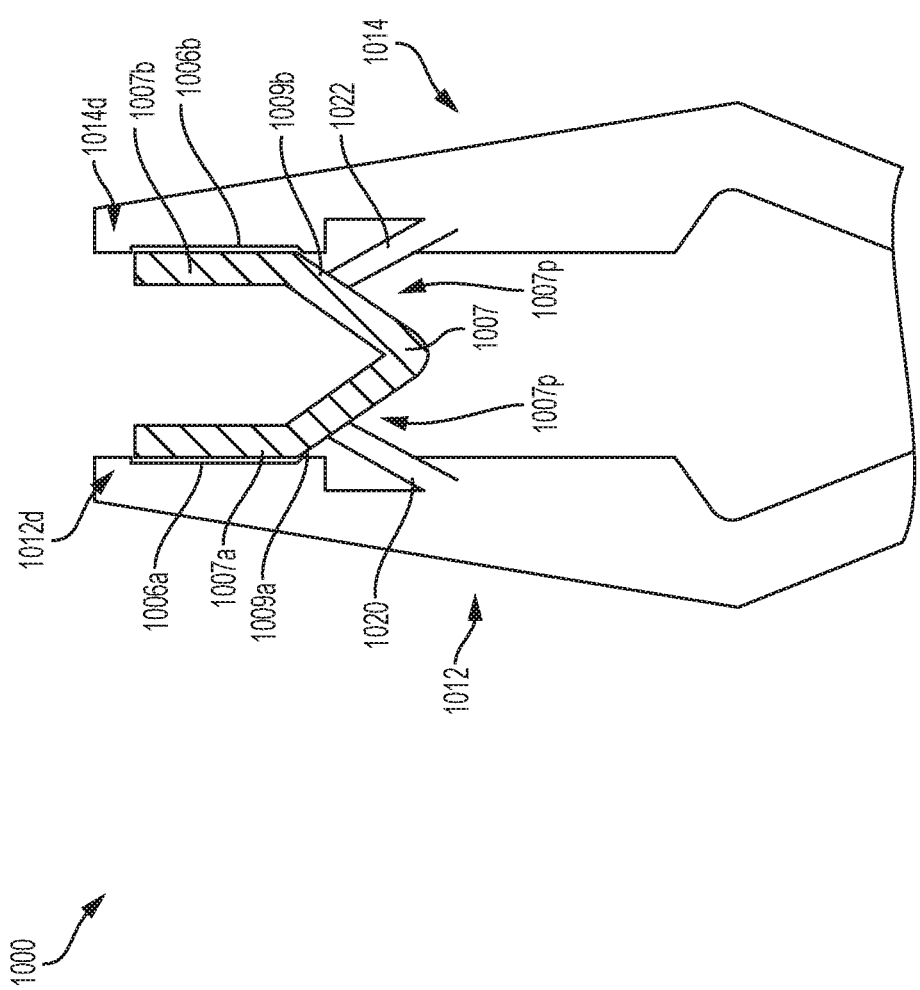

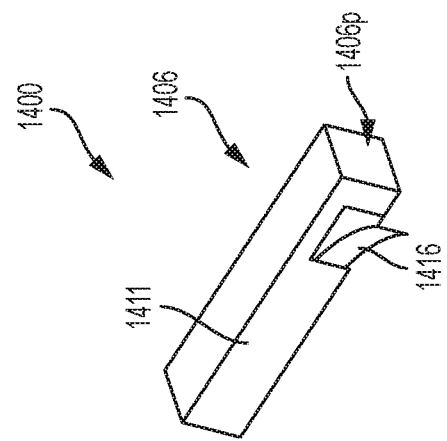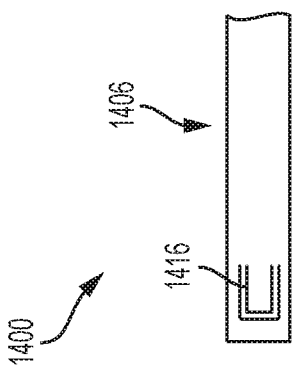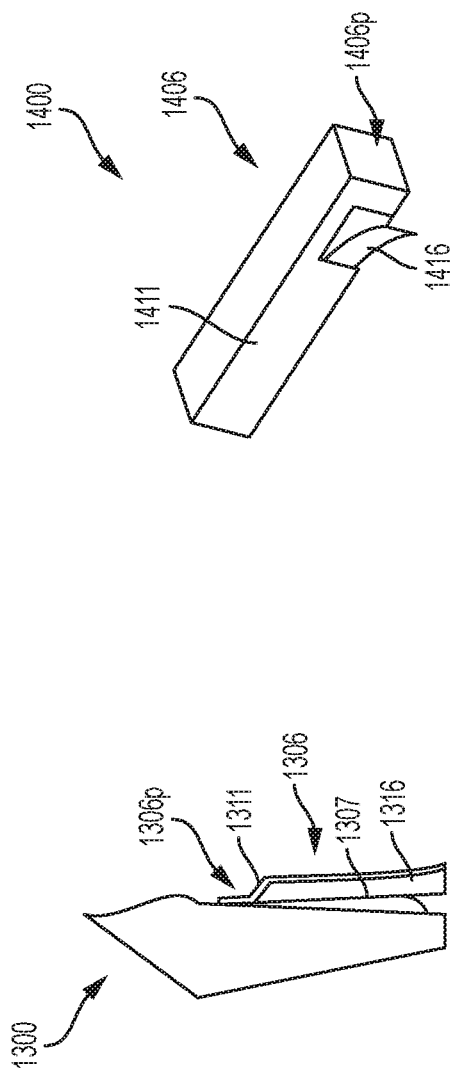

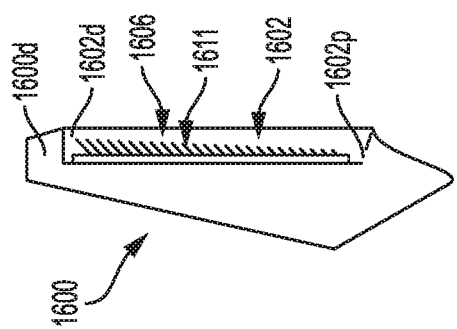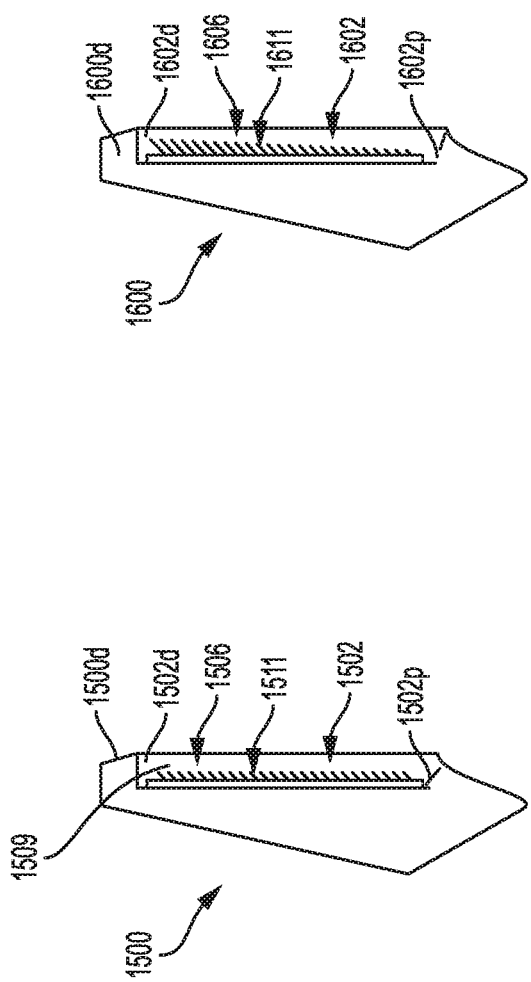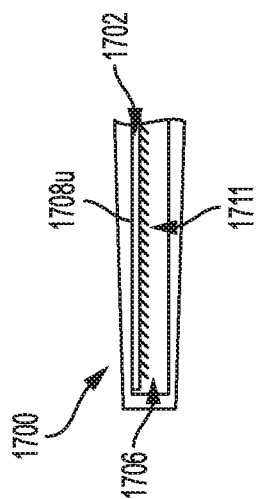

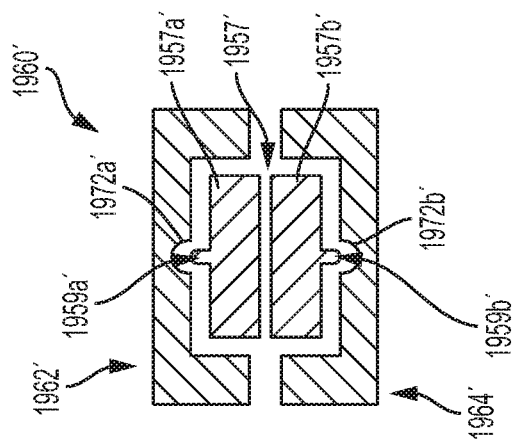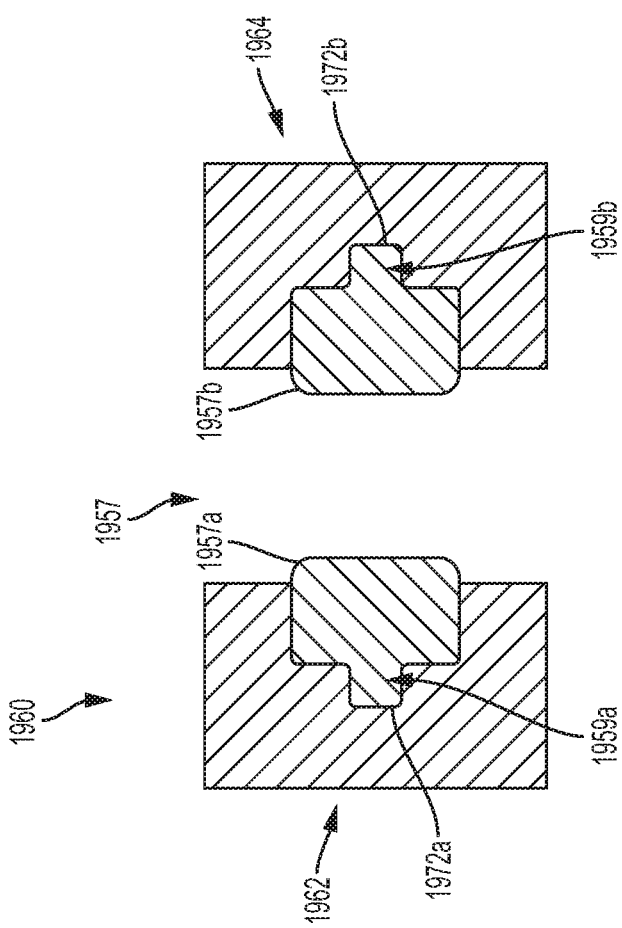
FIG. 25A
FIG. 25B

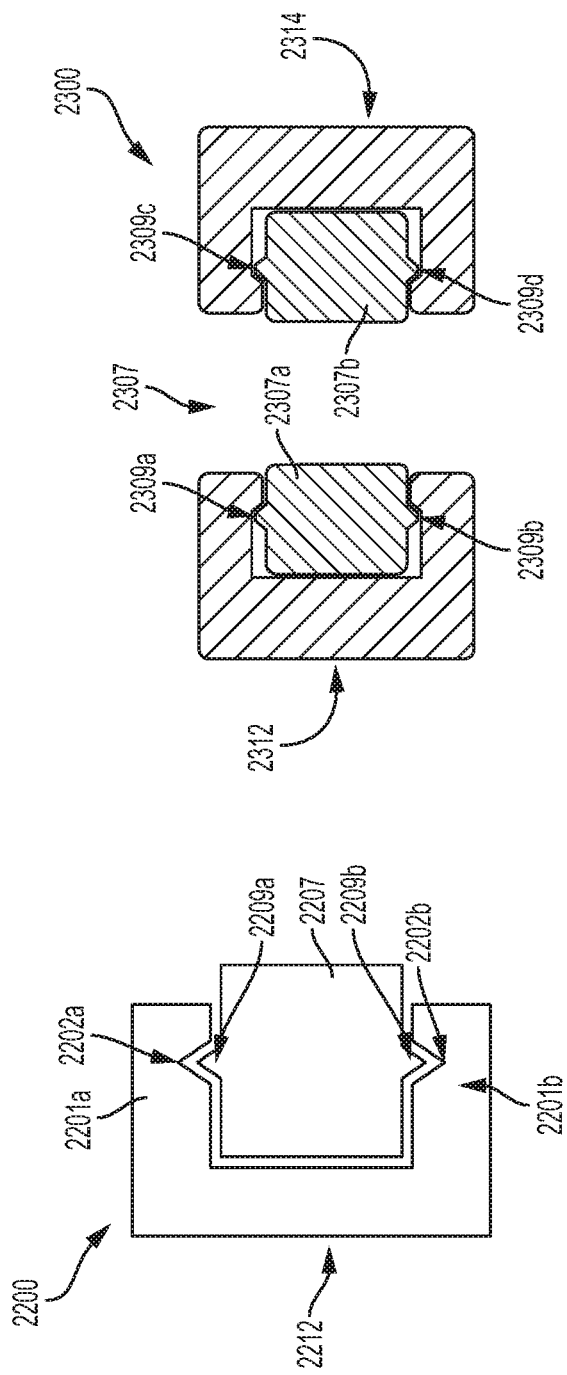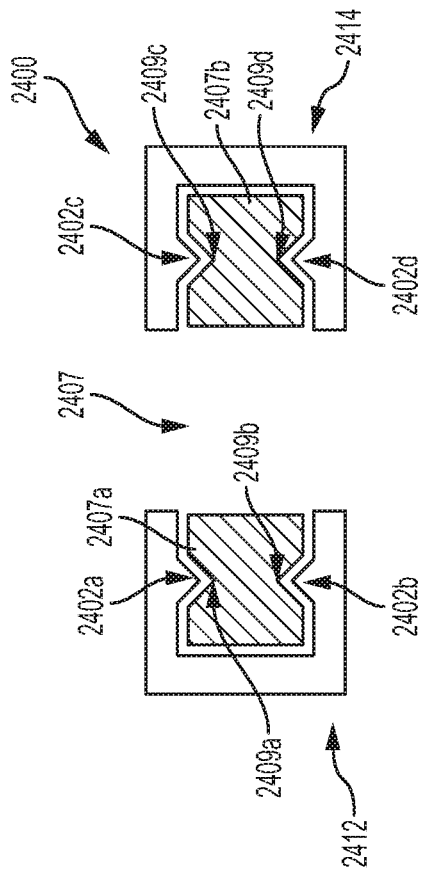
FIG. 26
FIG. 27
FIG. 28

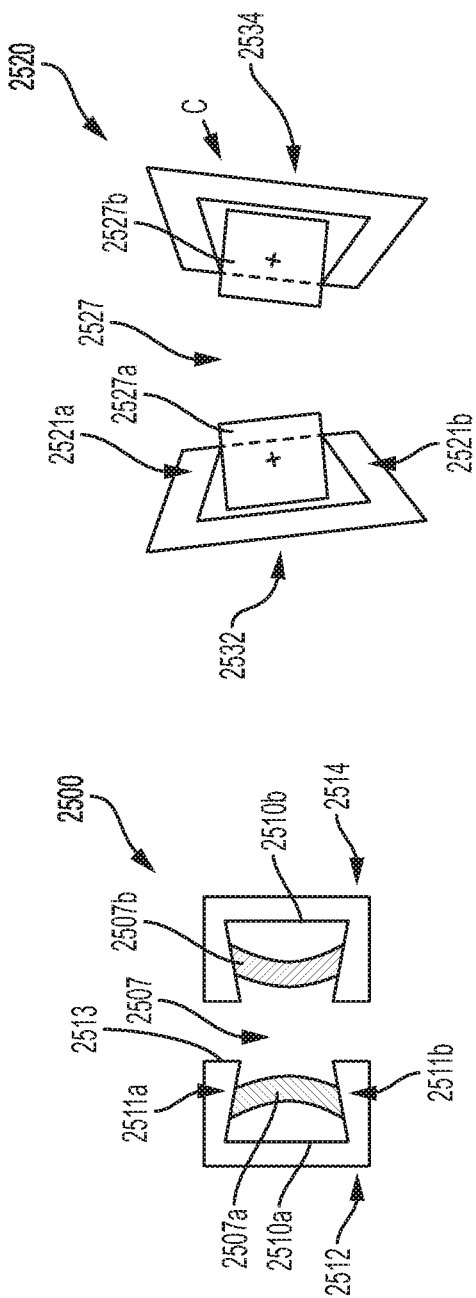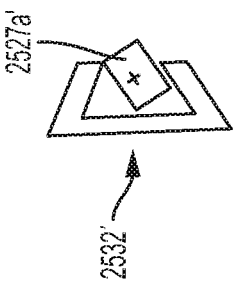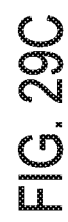
FIG. 29A
FIG. 29B
FIG. 29C

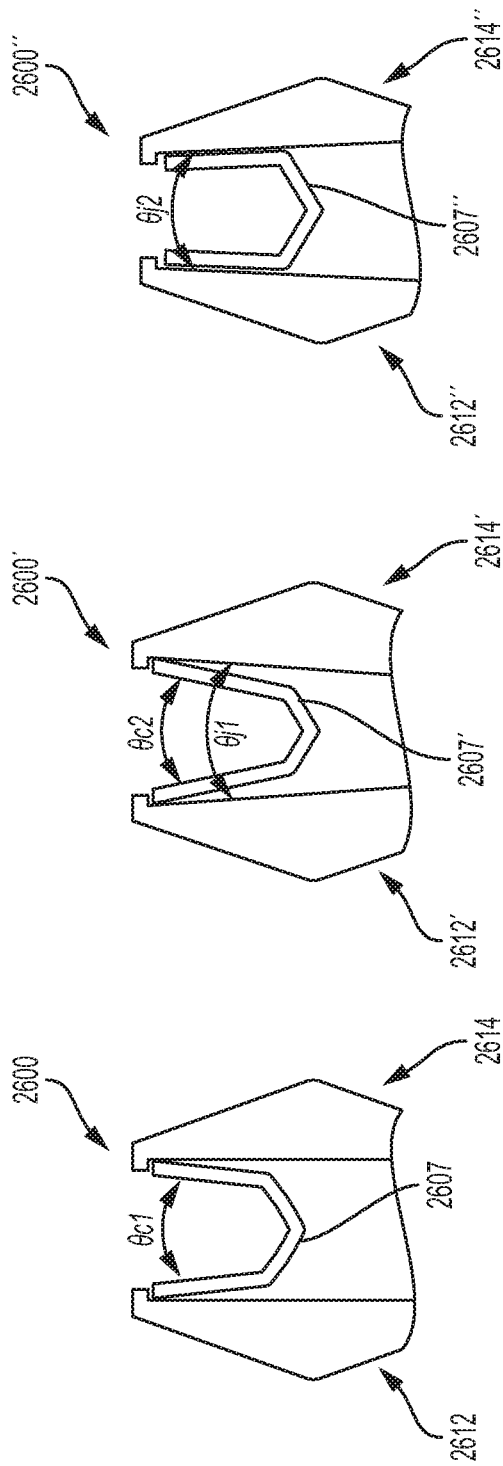

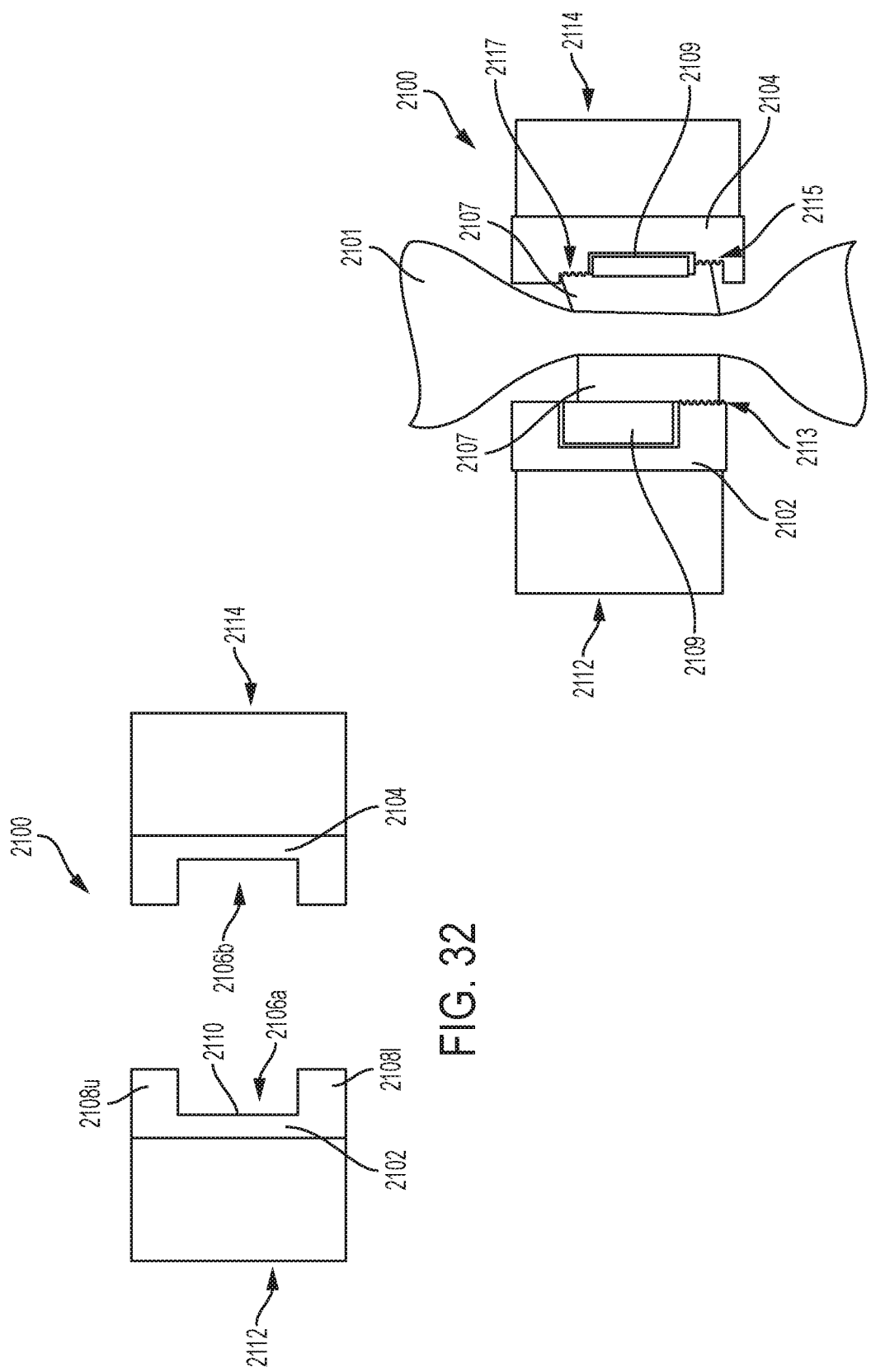

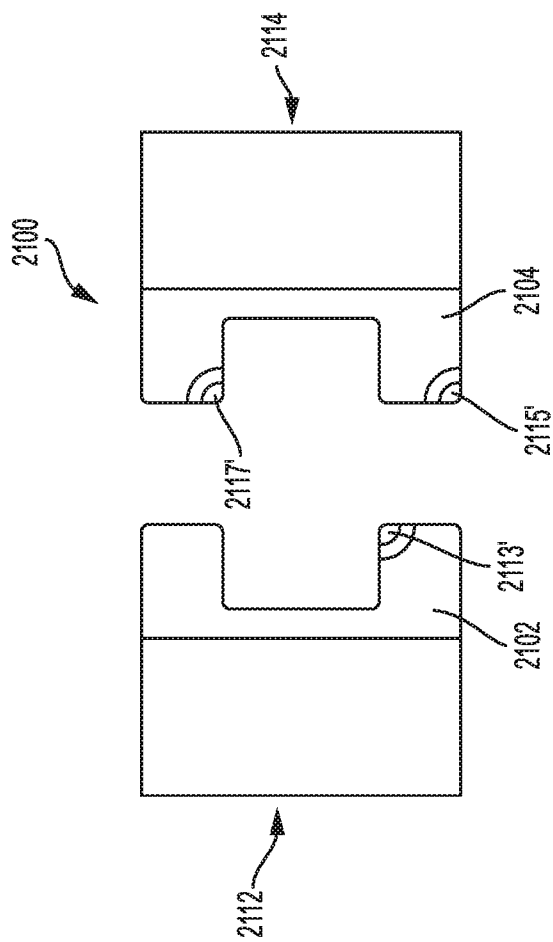

CLIP RETENTION FOR SURGICAL CLIP APPLIER

FIELD

Surgical clip applier devices and methods are provided having features for facilitating with clip retention.

BACKGROUND

Surgical clip appliers are commonly used for ligating a blood vessel, a duct, shunt, or a portion of body tissue during surgery. Most clip appliers typically have a handle with an elongate shaft having a pair of movable opposed jaws formed on an end thereof for holding and forming a ligation clip therebetween. The jaws are positioned around the vessel or duct, and the clip is crushed or formed on the vessel by the closing of the jaws.

One challenge with current clip appliers is retention of a clip within the jaws prior to and during clip formation. Many clip appliers advance a clip into the jaws when the trigger is released and/or during an initial phase of squeezing the trigger, and the jaws are released to return to the open configuration. As a result, the clip is pre-loaded in the jaws. Any movement or manipulation of the jaws could cause the clip to become misaligned, which can lead to clip malformation, or to fall out.

Accordingly, there remains a need for improved techniques for retaining surgical clips within the jaws of a surgical clip applier.

SUMMARY

Devices and method are provided for retention of a surgical clip within the jaws of a surgical clip applier. In at least one aspect, a surgical clip applier is provided that in some embodiments can include an elongate shaft and a clip advancing assembly extending through the elongate shaft. The elongate shaft can have first and second jaws on a distal end thereof that are movable between open and closed positions for engaging tissue therebetween. The clip advancing assembly can be configured to advance a stack of clips through the elongate shaft and to advance a distal-most clip into the first and second jaws. The first and second jaws can have opposed inward facing surfaces, with each inward facing surface having a clip guide channel formed there along for receiving and guiding legs of a clip into the first and second jaws. The clip guide channel on at least one of the first and second jaws can include at least one deflectable clip retention member disposed therein and configured to apply a biasing force to a leg of a clip disposed within the first and second jaws to thereby retain the clip within the first and second jaws.

The surgical clip applier can vary in many ways. For example, the at least one deflectable clip retention member can apply the biasing force to a leg of a clip a direction substantially perpendicular to a plane extending through the first and second jaws. As another example, the at least one deflectable clip retention member can apply the biasing force to a leg of a clip a direction of a plane extending through the first and second jaws.

In some embodiments, the at least one deflectable clip retention member can extend along a longitudinal length of at least one of the first and second jaws and the biasing force applied by the at least one deflectable clip retention member can vary along the longitudinal length. In some embodiments, the at least one deflectable clip retention member can be elastically deformable. For example, the at least one deflectable clip retention member can be or can include a leaf spring.

The clip guide channel of the surgical clip applier can also vary in many ways. For example, the clip guide channel can include an upper surface, a lower surface, and a sidewall extending between the upper and lower surfaces. The at least one deflectable clip retention member can be disposed on the sidewall and can bias a leg of a clip toward the opposed jaw. As another example, the clip guide channel can include an upper surface, a lower surface, and a sidewall extending between the upper and lower surfaces, and the at least one deflectable clip retention member can include a first deflectable clip retention member disposed on the upper surface and a second deflectable clip retention member disposed on the lower surface such that the first and second deflectable clip retention members engage a leg of a clip therebetween. As another example, the clip guide channel can further include at least one deflectable tab configured to engage a proximal surface of a clip after the clip moves distally past the at least one deflectable tab.

The at least one deflectable clip retention member can be made from any suitable material(s). In some embodiments, at least a portion of the at least one deflectable clip retention member can be formed from a self-healing material.

In another aspect, a surgical clip applier is provided that in some embodiments can include an elongate shaft with first and second jaws on a distal end thereof, and a clip advancing assembly extending through the elongate shaft. The first and second jaws can be movable between open and closed positions for engaging tissue therebetween, and the first and second jaws can have inward facing surfaces defining a clip track for receiving and guiding a clip into the jaws. At least one compressible clip retention member can be disposed within the clip track in one of the first and second jaws. The clip advancing assembly can extend through the elongate shaft and it can be configured to distally advance a plurality of clips through the elongate shaft and to advance a distal-most clip of the plurality of clips into the clip track in the first and second jaws. The at least one clip retention member can be configured to move from a first, uncompressed configuration to a second, compressed configuration when the distal-most clip is advanced into the clip track.

The at least one clip retention member of the surgical clip applier can vary in many ways. For example, a distal portion of the at least one clip retention member can be more flexible than a proximal portion of the at least one clip retention member. As another example, the at least one clip retention member can be disposed on a sidewall of the clip track, with the sidewall extending between upper and lower walls of the clip track. As a further example, the at least one clip retention member can be disposed on at least one of an upper wall, a lower wall, and a sidewall of the clip track, with the sidewall extending between the upper and lower walls.

In some embodiments, the at least one clip retention member can include a first retention member disposed on an upper wall of the clip track and a second retention member disposed on a lower wall of the clip track such that the first and second retention member are configured to engage a leg of a clip therebetween. In some embodiments, the at least one clip retention member can be or can include a leaf spring extending longitudinally along at least one of the first and second jaws.

In some embodiments, the clip track can include at least one deflectable tab configured to engage a proximal surface of a clip after the clip moves distally past the at least one deflectable tab.

The clip retention members can be made from any suitable material(s). In some embodiments, a portion of at least one of the clip retention members be formed from a self-healing material, such as a poly(urea-urethane).

In another aspect, a method for applying a surgical clip to tissue is provided that in some embodiments can include manipulating first and second jaws on a clip applier to position tissue between the first and second jaws, and actuating the clip applier to move the first and second jaws from an open position to a closed position to deform a clip positioned within a clip track formed in each of the first and second jaws and thereby engage the tissue between legs of the clip. At least one resilient clip retention member disposed within the clip track in at least one of the first and second jaws can apply a biasing force to the clip to maintain the clip in alignment with the first and second jaws as the jaws are moved from the open position to the closed position.

The method can vary in many ways. For example, at least one deflectable tab in the clip track can prevent proximal movement of the clip within the clip track.

BRIEF DESCRIPTION OF THE DRAWINGS

The present disclosure will be more fully understood from the following detailed description taken in conjunction with the accompanying drawings, in which:

FIG. 5A is another perspective view of a distal portion of the surgical clip applier of FIG. 1;

FIG. 5B is a perspective view of a clip that can be disposed between the jaws of the surgical clip applier of FIG. 5A;

FIG. 9A is a perspective, partial view of another embodiment of a jaw of a surgical clip applier showing the deflectable clip retention member disposed on the lower surface of the clip guide channels;

FIG. 9B is a cross-sectional, partial view of the jaw of FIG. 9A, showing the deflectable clip retention members disposed on the lower and upper surfaces of the clip guide channels, in a compressed configuration with a clip disposed within the jaws;

FIG. 14A is a perspective, partially transparent view of an embodiment of first and second jaws of a surgical clip applier having clip retention members staggered along the longitudinal axis on upper and lower surfaces of a clip guide channel of each of the jaws;

FIG. 14B is a side, partially transparent view of the first jaw FIG. 14A;

FIG. 15 is a top schematic view of an embodiment of jaws of a surgical clip applier having deflectable tabs;

FIG. 18 is a top view of an embodiment of a jaw of a surgical clip applier having a clip track with a deformable tab;

FIG. 19A is a perspective view of an embodiment of a clip track of a jaw of a surgical clip applier having a deformable tab;

FIG. 19B is another perspective view of the clip track of FIG. 19A;

FIG. 20 is a top schematic view of an embodiment of a jaw of a surgical clip applier having a clip track with flexible extensions;

FIG. 21 is a top schematic view of another embodiment of a jaw of a surgical clip applier having a clip track with flexible extensions;

FIG. 22 is a top schematic view of yet another embodiment of a jaw of a surgical clip applier having a clip track with flexible extensions;

FIG. 25A is a lateral cross-sectional view of an embodiment of jaws of a surgical clip applier each having a female mating feature configured to mate with a corresponding male mating feature of a surgical clip;

FIG. 25B is a lateral cross-sectional view of an embodiment of jaws of a surgical clip applier each having a female mating feature configured to mate with a corresponding male mating feature of a surgical clip;

FIG. 26 is a cross-sectional view of an embodiment of a jaw a surgical clip applier having female mating features on upper and lower rails thereof that are configured to mate with corresponding male mating features of a surgical clip;

FIG. 27 is a lateral cross-sectional view of an embodiment of jaws of a surgical clip applier and a surgical clip having first and second legs, showing that the first and second legs of the clip each having small protrusions configured to facilitate retention of the clip by the jaws;

FIG. 28 is a lateral cross-sectional view of an embodiment of jaws of a surgical clip applier and a surgical clip having first and second legs, showing the first and second legs of the clip each having female mating features configured to mate with corresponding male mating features of the jaws;

FIG. 29A is a lateral cross-sectional view of an embodiment of jaws of a surgical clip applier and a surgical clip having first and second legs, showing the first and second legs of the clip being reversibly deformable when the clip is advanced between the jaws;

FIG. 29B is a lateral cross-sectional view of an embodiment of jaws of a surgical clip applier and a surgical clip having first and second legs, showing the jaws being reversibly deformable and shaped so as to deformably retain the first and second legs of the clip;

FIG. 29C is a lateral cross-sectional view of an embodiment of a jaw of a surgical clip applier and a leg of a surgical clip, the jaw being reversibly deformable and shaped so as to deformably retain the leg of the clip, wherein the clip's leg is shown retain by the jaw when the clip unintentionally rotates during the clip formation;

FIG. 30A is a longitudinal top view of one embodiment of first and second jaws of a surgical clip applier, where the first and second jaws are substantially parallel to one another, and where a surgical clip is shown disposed between the jaws, the clip having first and second legs that are disposed at an obtuse angle with respect to one another;

FIG. 30B is a longitudinal top view of another embodiment of first and second jaws of a surgical clip applier, where the first and second jaws are disposed at an obtuse angle with respect to one another, and where a surgical clip is shown disposed between the jaws, the clip having first and second legs that are disposed at an obtuse angle with respect to one another;

FIG. 30C is a longitudinal top view of another embodiment of first and second jaws of a surgical clip applier, where the first and second jaws are disposed at an acute angle with respect to one another, and where a surgical clip is shown disposed between the jaws, the clip having first and second legs that are substantially parallel to one another;

FIG. 30D is a longitudinal top view of another embodiment of first and second jaws of a surgical clip applier, where the first and second jaws are proximally tapered, and where a surgical clip is shown disposed between the jaws, the clip having first and second legs that are also proximally tapered;

FIG. 32 is a schematic cross-sectional view of one embodiment of jaws of a surgical clip applier having a self-healing material;

FIG. 33 is another schematic cross-sectional view of the jaws of the surgical clip applier of FIG. 32, showing damage incurred to the jaws when the jaws apply a surgical clip over another clip previously formed on a tissue; and FIG. 34 is another schematic cross-sectional view of the jaws of the surgical clip applier of FIG. 32, showing the jaw after damages are incurred and after self-healing.

DETAILED DESCRIPTION

Figure 1:
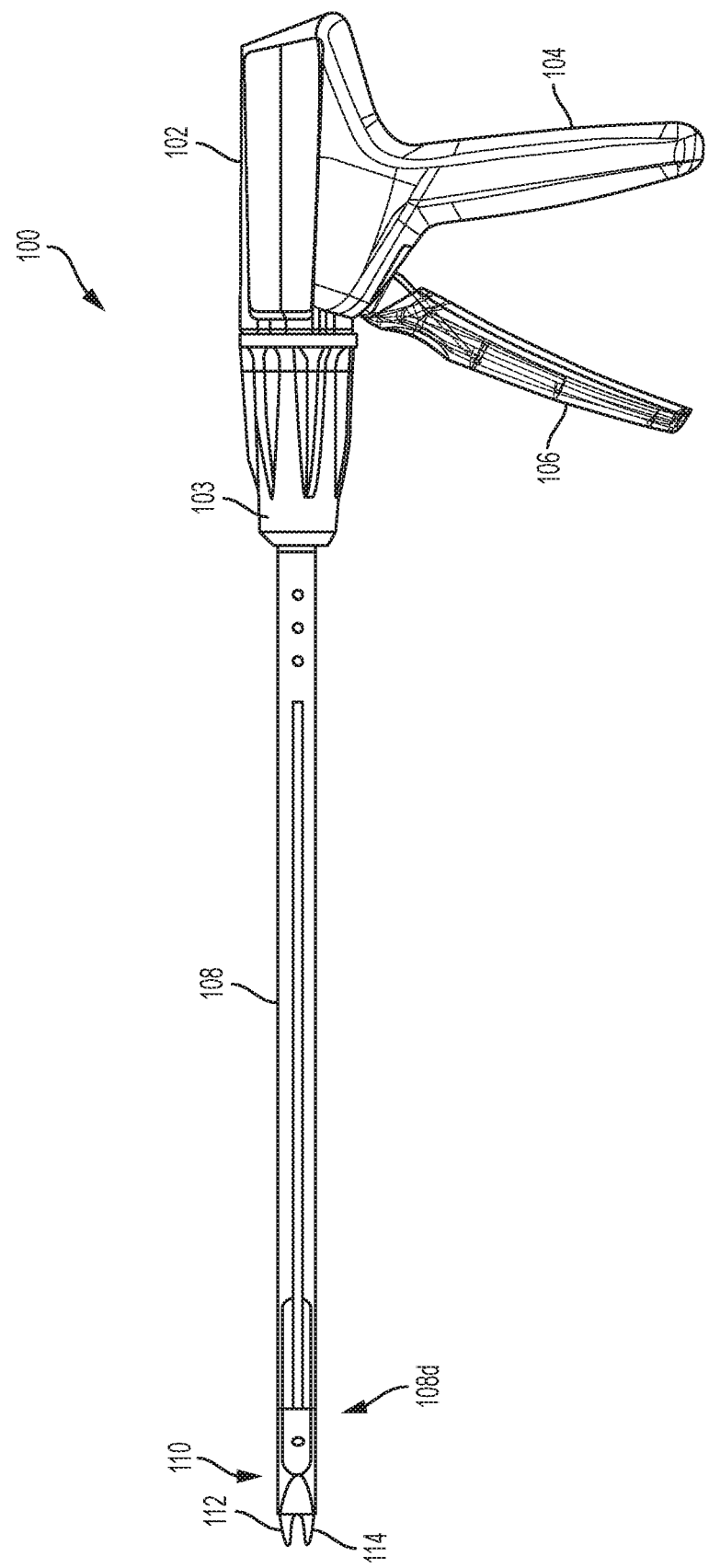
FIG. 1 is a side view of one exemplary embodiment of a surgical clip applier.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Surgical clip appliers having first and second jaws, and methods for using a surgical clip applier apply surgical clips to a vessel, duct, shunt, etc., during a surgical procedure, are provided herein. At least one of the jaws of the surgical clip applier can include at least one clip retention member configured to retain a surgical clip between the jaws such that alignment of the clip with respect to the jaws is maintained. The at least one clip retention member can be formed on, within, or coupled to a clip track defined in an inward facing surface of the jaw, and the at least one clip retention member can apply a biasing force to a clip when a clip is disposed between the jaws. The clip retention member can have many different forms, and the jaw(s) can include multiple clip retention members on one or more surfaces thereof or coupled thereto.

FIGS. 1-4B illustrate one embodiment of a surgical clip applier 100. As shown, the surgical clip applier 100 generally includes a housing 102 having a stationary handle 104 and a movable handle or trigger 106 that is pivotally coupled to the housing 102. An elongate shaft 108 extends distally from the housing 102 and includes a jaw assembly 110 formed on a distal end 108d thereof and including first and second jaws 112, 114 that are movable between open and closed positions. The first and second jaws 112, 114 include opposed inward facing surfaces and each inward facing surface has a clip track formed therealong for receiving and guiding legs of a clip into the first and second jaws 112, 114. The elongate shaft 108 can be rotated with respect to the housing 102 via a rotation knob 103.

Figure 2:
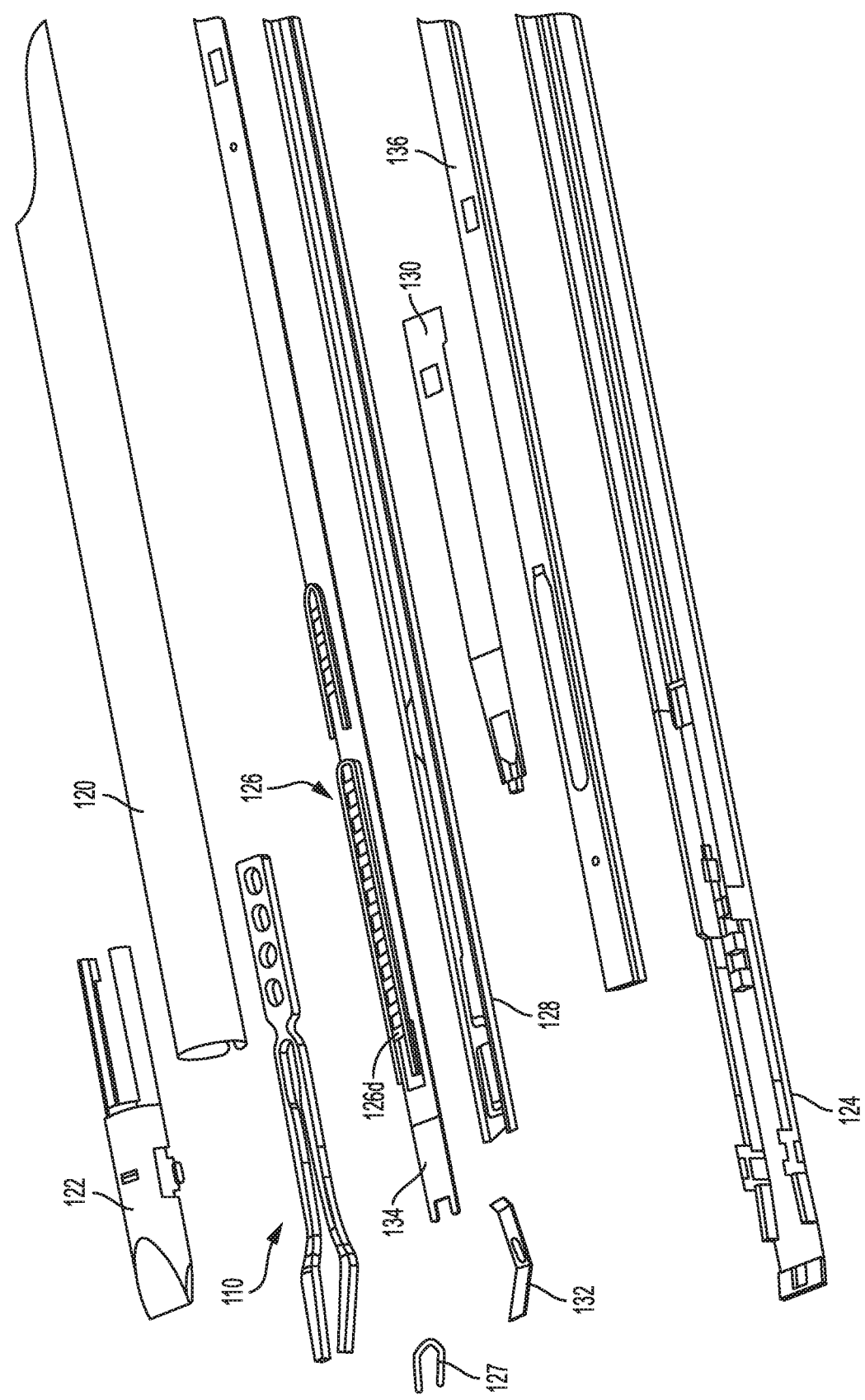
FIG. 2 is an exploded view of a distal portion of the surgical clip applier of FIG. 1.
Figure 3:
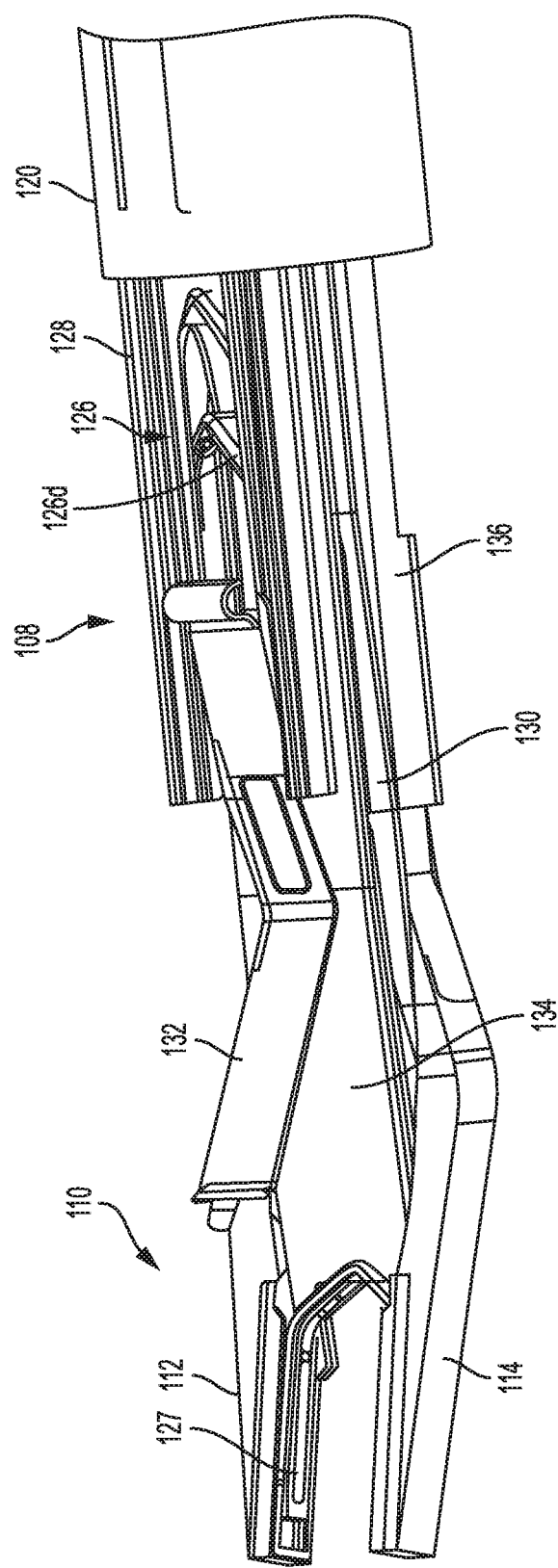
FIG. 3 is a perspective view of a distal portion of the surgical clip applier of FIG. 1.

As shown in FIGS. 2 and 3, the elongate shaft 108 can include an outer support tube 120, an upper shroud 122 coupled distally to the outer support tube 120, and a lower shroud 124. The outer support tube 120 and the upper and lower shrouds 122, 124 form an outer casing of the shaft 108. As shown in FIGS. 2 and 3, a clip stack 126 including multiple surgical clips is disposed within a clip track or holder 128 of the shaft 108 proximal to the first and second jaws 112, 114, and is biased distally. A floor 130 extends beneath the clip stack 126 for maintaining the clip stack 126 in alignment within the shaft 108, and for guiding a distal-most clip 126d into the jaws 112, 114. A lifter spring 132 is positioned just proximal to the jaws 112, 114 and distal to the clip stack 126 for preventing distal movement of the clip stack 126, with the distal-most clip 126d disposed around the lifter spring 132. A feeder bar 134 extends through the elongate shaft 108 for feeding the distal-most clip 126d into the jaws. As shown in FIG. 3 illustrating the clip applier 100 with the upper and lower shrouds 122, 124 removed, a former tube 136 extends around a proximal end of the jaws 112, 114 and is movable distally to cam the jaws 112, 114 to a closed position for forming a clip 127 disposed therebetween.

Figure 4A:
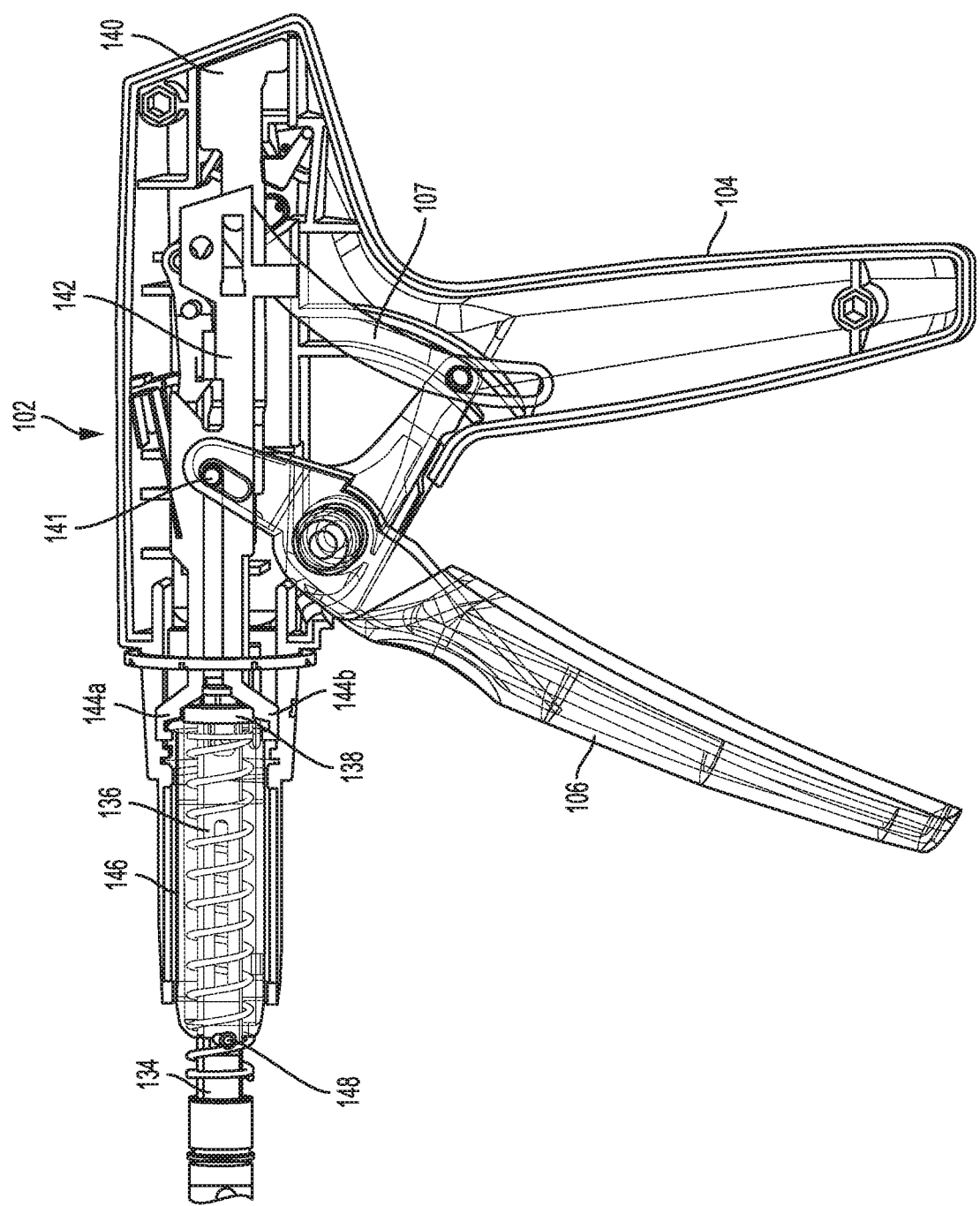
FIG. 4A is a perspective, partially transparent view of a proximal portion of the surgical clip applier of FIG. 1.
Figure 4B:
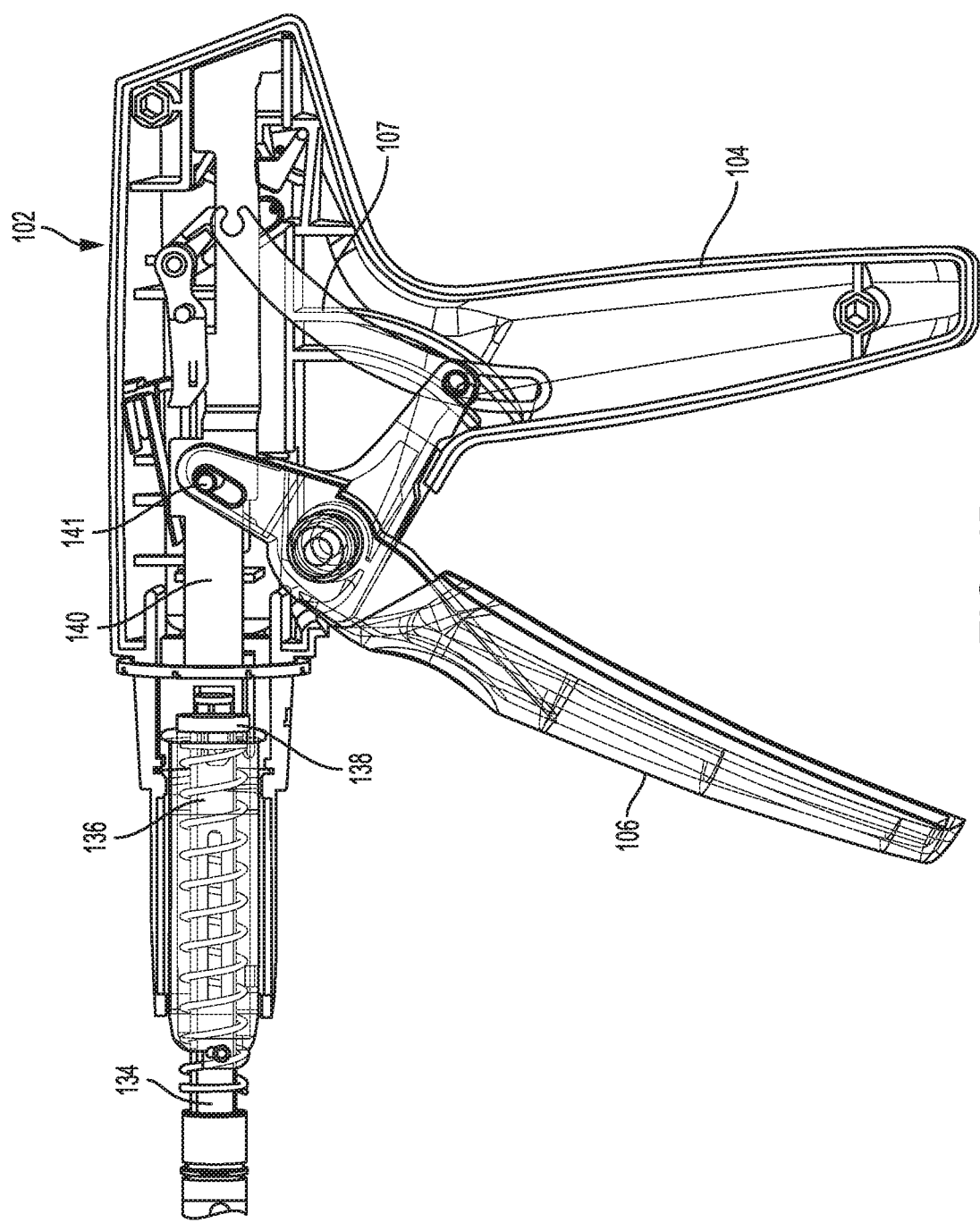
FIG. 4B is another perspective view of the proximal portion of the surgical clip applier of FIG. 1.

The surgical clip applier 100 has a clip forming assembly including various components that operate together to close the jaws 112, 114 when the trigger 106 is activated to thereby cause a clip (e.g., clip 127) disposed in the jaws to be applied (formed) to the tissue. The clip forming assembly encompasses the former tube 136 and other components that are coupled to the trigger 106 configured to be activated to move the former tube 136 distally to thereby close the jaws 112, 114. A clip advancing assembly of the surgical clip applier 100 includes the feeder bar 134 that is also coupled to the trigger 106, via a link 107 extending proximally from the trigger 106, as shown in FIGS. 4A and 4B. In this way, when the trigger 106 is activated, the feeder bar 134 is caused to move proximally, opposite to a distal direction in which the former tube 136 is moved upon activation of the trigger 106.

The clip forming and clip advancing assemblies can have any suitable configurations. For example, in the illustrated embodiment, as shown in FIGS. 4A and 4B, the former tube 136 of the clip forming assembly is coupled, via an inner coupling 138, to a former plate 140 in the handle 104 that is, in turn, coupled to the trigger 106 via a pin 141, and the feeder bar 134 of the clip advancing assembly is coupled to the trigger 106 via a feeder plate 142 that is also coupled to the trigger 106, via the link 107. As shown in FIG. 4A, the feeder plate 142 has arms 144a, 144b at a distal end thereof that are disposed over and mate with a proximal end of an outer coupling 146 (shown partially transparent). A connecting pin 148 at a distal end of the outer coupling 146 attaches the feeder bar 134 to the outer coupling 146. FIGS. 4A and 4B illustrate the handle 104 with part of an outer casing removed, and FIG. 4B shows the handle 104 without the feeder plate 142, for illustration purposes only. It should be appreciated that the surgical clip applier 100 can include various other components and assemblies that are not described herein for the sake of simplicity.

In use, when the trigger 106 of the handle 104 is activated (e.g., moved towards the stationary handle 104), the former plate 140 of the clip forming assembly is advanced distally to cause the former tube 136 to advance distally over the jaws 112, 114, thereby camming the jaws 112, 114 to the closed position. At the same time, the feeder plate 142 of the clip advancing assembly is moved proximally, thereby pulling the feeder bar 134 proximally to position the feeder bar 134 proximal of the distal-most clip 126d of the clip stack 126. Once the clip 127, disposed in the jaws 112, 114 such that clip's legs are received within the clip track of each of the jaws, is fully formed, the trigger 106 is released, which causes the clip forming assembly to move proximally while the clip advancing assembly moves distally. FIG. 2 shows the clip 127 in an original, pre-formed configuration. The proximal movement of the clip forming assembly causes the former tube 136 to retract relative to the jaws, thus allowing the jaws 112, 114 to move to the original open position, thereby releasing the formed clip. The distal movement of the clip advancing assembly causes the feeder bar 134 to move distally, and the feeder bar 134 thereby pushes the distal-most clip 126d distally, overcoming the biasing force of the lifter spring 132 and causing the lifter spring 132 to deflect out of the way, thereby allowing the distal-most clip 126d to be advanced into the jaws 112, 114. In this way, the distal-most clip becomes positioned in the jaws' clip track, like the clip 127 in FIG. 3. The floor 130 helps guide the distal-most clip into the clip tracks of the jaws 112, 114.

A person skilled in the art will appreciate that, while a trigger is shown and described, the clip appliers disclosed herein need not include a trigger, and can have a variety of other actuation mechanisms. For example, the clip applier can be powered and can include an actuation button for actuating a motor to control firing of the device. In other embodiments, the housing can be configured to couple to a robotic or tele-manipulator system, such that actuation of the device is controlled through the robotic or tele-manipulator system.

As mentioned above, each of the first and second opposed jaws 112, 114 of the surgical clip applier 100 include opposed inward facing surfaces 203, 205, as shown in more detail in FIG. 5A. The opposed inward facing surfaces 203, 205 can each define a clip track for receiving and guiding a clip into the jaws. The clip track, which can be in the form of a clip guide channel, receives the distal-most clip from the clip stack 126 disposed within a shaft 108. As shown in FIG. 5A, each inward facing surface 203, 205 has a clip guide channel formed there along for receiving and guiding legs 207a, 207b of a clip 207 (shown separately in FIG. 5B) into the first and second jaws 112, 114. The clip 207 can be similar to the clip 127 in FIGS. 2 and 3, or it can have other configurations. The inward facing surface 203 of the first jaw 112 includes a clip guide channel 206, while a clip guide channel of the inward facing surface 205 of the opposed jaw 114 is obscured. As further shown in FIG. 5A, the clip guide channel 206 is defined by an upper rail 208u, a lower rail 208l, and a sidewall 210 extending between the upper and lower rails 208u, 208l. When the clip 207 is advanced from the shaft 108 into the jaws 112, 114, the clip 207 is positioned in the manner as shown in FIG. 3.

While the upper and lower rails 208u, 208l may help retain the clip within the clip track, proper retention of a clip by the jaws of a surgical clip applier may pose a challenge. In order to accommodate manufacturing variances in the clips, the clip track can be sized to provide a certain amount of clearance therein. This can result in inadequate grip of the clip by the jaws, and the clip can thus become tilted or otherwise improperly positioned with respect to the clip track. Such insufficient clip-to-jaw retention can lead to clip malformation (e.g., scissoring), premature clip ejection, or other undesirable consequences which can compromise a surgical procedure.

Accordingly, techniques are provided for ensuring proper retention of a clip with the jaws of a surgical clip applier. In particular, as mentioned above, in some embodiments, at least one of the jaws of a surgical clip applier can include at least one deflectable clip retention member disposed therein. The clip retention member can be configured to apply a biasing force to a leg of a clip disposed within the jaws to thereby retain the clip within the jaws. In this way, when a clip is advanced to be seated between the jaws, the retention member(s) can move from a first, uncompressed configuration to a second, compressed configuration. In at least some embodiments, the biasing force applied by the clip retention member(s) can compensate for differences in sizes between the clip and the jaws, thereby securely retaining the clip between the jaws.

The clip retention member(s) can have various configurations and can be positioned on a jaw of a surgical clip in various ways. For example, the clip retention member can be formed on or coupled to the jaw at one or more locations along the inward facing surfaces of the jaws. One or more clip retention members can be disposed on a sidewall of the clip guide channel, on one or both of the upper and lower rails of the clip guide channel, or in any other portions of the jaw.

Figure 6:
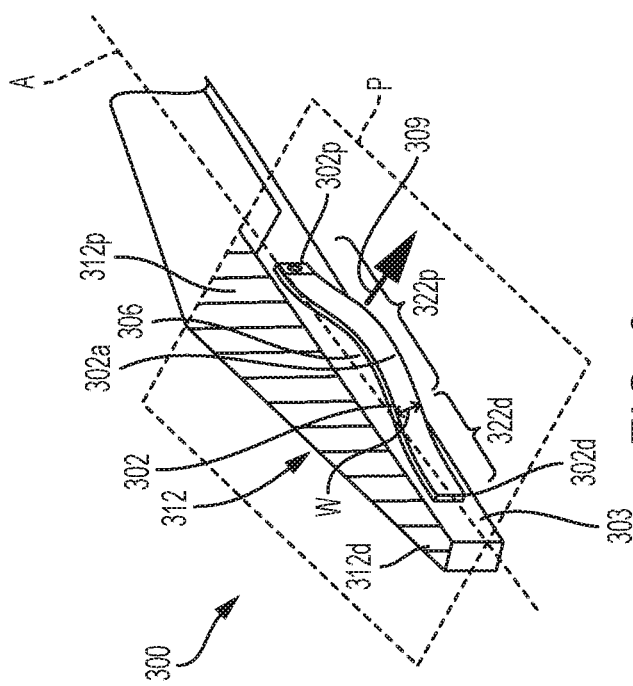
FIG. 6 is a perspective, partial view of an embodiment of a jaw of a surgical clip applier having a deflectable clip retention member.
Figure 8:
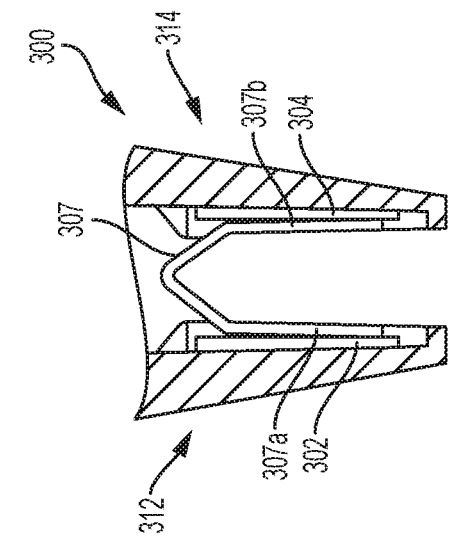
FIG. 8 is a top perspective, partial view of the jaws of the surgical clip applier of FIG. 7, showing the deflectable clip retention member in a compressed configuration when a clip is disposed between the jaws.
Figure 7:
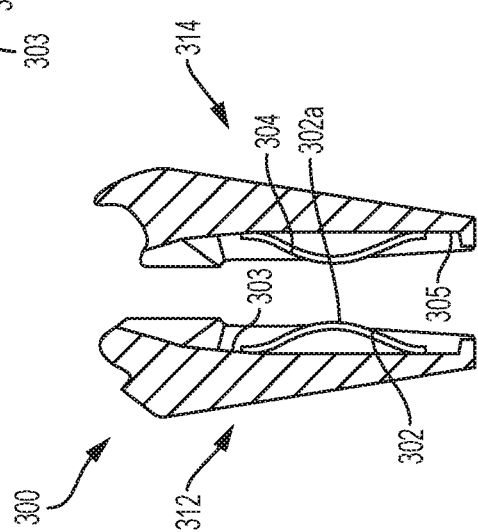
FIG. 7 is a top perspective, partial view of jaws of the surgical clip applier of FIG. 6, showing the deflectable clip retention member in an uncompressed configuration.

FIG. 6 illustrates one embodiment of a deflectable clip retention member 302 positioned on an inward facing surface 303 of a first jaw 312 of a surgical clip applier 300, with the opposed jaw 314 having a deflectable clip retention member 304 on it's inward facing surface 305, as shown in FIGS. 7 and 8. The clip retention member 302 extending along the inward facing surface 303 can be disposed in a clip track or clip guide channel 306 formed in the inward facing surface 303. It should be appreciated that, although not shown in FIG. 6 for the sake of simplicity, the clip guide channel 306 can be configured similar to clip guide channel 206 (FIG. 5A), such that the clip guide channel 306 can have an upper rail, a lower rail, and a sidewall extending between the upper and lower rails. The clip retention member 302 can be formed on or disposed on the sidewall of the clip guide channel 306 such that the clip retention member 302 biases a leg of a clip toward the opposed jaw. The clip retention member 302 can extend along a longitudinal length of the jaw 312 and can be configured to move from a first, uncompressed configuration to a second, compressed configuration when a distal-most clip is advanced into the clip guide channel 306.

The clip retention member 302 of FIG. 6 can have various configurations, and it can be coupled to the inward facing surface 303 of the jaw 312 in various ways. In the illustrated embodiment, the clip retention member 302 is in the form of an elongate leaf spring coupled to the sidewall of the clip guide channel 306 on surface 303 in a suitable manner. A width W of the clip retention member 302 (shown in FIG. 6) can be the same or substantially the same along its length. In at least some embodiments, the width can be less than a height of the clip guide channel 306. Further, in this example, as shown in FIG. 6, the clip retention member 302 can be positioned such that its distal end 302d is offset proximally from a distal end 312d of the jaw 312. As also shown, a proximal end 302p of the clip retention member 302 can be coupled to the inward facing surface 303 at a proximal end 312p of the jaw 312. The proximal end 302p can include one, two, or more discrete attachment points, or the entire area of the proximal end 302p of the clip retention member 302 can be coupled to the jaw's inward facing surface 303. In FIG. 6, a distal end 302d of the clip retention member 302 is not coupled to the jaw's facing surface 303, and contacts and is biased against the surface 303. As a result, the distal end 302d is freely movable and can slide distally when the clip retention member 302 deflects. It should be appreciated, however, that the clip retention member can be coupled to the inward facing surface of the jaw in more than one location. For example, in some embodiments, both the proximal and distal ends 302p, 302d ends of the clip retention member 302 can be coupled to the inward facing surface 303 in any suitable manner, or alternatively only the distal end 302d can be coupled to the inward facing surface 303.

As shown in FIGS. 6 and 7, in an uncompressed configuration, the clip retention member 302 disposed on the jaw 312 is curved towards the opposed jaw, such that a middle portion 302a of the clip retention member 302 is positioned farthest away from the inward facing surface 303. It should be appreciated that the clip retention member 302 can be configured to have one (as in this example) or more curves in the uncompressed configuration.

FIG. 7 illustrates both of the clip retention members 302, 304 on the opposed inward facing surfaces 303, 305 of the jaws 312, 314, respectively. When a surgical clip 307 is advanced so as to be positioned between the jaws 312, 314, the clip retention members 302, 304 apply a biasing force to legs 307a, 307b of the clip 307, respectively. When the clip 307 is disposed between the jaws 312, 314 having the respective the clip retention members 302, 304, the clip retention members 302, 304 move from the first, uncompressed configuration to a second, compressed configuration as shown in FIG. 8. In this configuration, the biasing force applied to the clip 307 by the clip retention members 302, 304 will help securely retain the clip within the jaws. Once positioned between the jaws 312, 314, the clip 307 can be formed. As disused above in connection with FIGS. 1-4B, as the jaws 312, 314 are approximated to clamp tissue therebetween and form the clip disposed therein, a subsequent clip of a clip stack (e.g., clip stack 126 in FIGS. 2 and 3) can be advanced by a clip advancing assembly to be positioned between the jaws 312, 314.

In the embodiment shown in FIGS. 6, 7, and 8, the clip retention member 302 on the first jaw 312, as well as the clip retention member 304 on the opposed second jaw 314, can be configured to apply the biasing force to a respective leg of the clip a direction (shown by arrow 309 in FIG. 6) of a plane P (FIG. 6) extending through the first and second jaws 312, 314. The lateral loads applied by the clip retention members 302, 304 on the clip legs 307a, 307b improve clip retention by the jaws 312, 314.

The clip retention member 302, discussed as a representative of the clip retention members 302, 304, can be configured to apply the biasing force in any desired manner. For example, the clip retention member 302 can be configured to apply the biasing force with the same or substantially the same strength along the length of the jaw. However, in some embodiments, the biasing force applied by the clip retention member 302 can vary along the longitudinal length of the jaw 312. The biasing force can vary in a suitable manner along a longitudinal axis A of the jaw 312 shown in FIG. 6. For example, as schematically shown in FIG. 6, a distal portion 322d of the clip retention member 302 can be more flexible than a proximal portion 322p of the clip retention member 302. This can help maintain legs of a clip at a desired distance from one another when the clip is formed and to decrease a possibility of deformation of the clip.

It should be appreciated that the distal and proximal portions 322d, 322p of the clip retention member 302 are shown by way of example, as the distal and proximal portions can have any suitable lengths, including the same or different lengths. In at least one embodiment, as in the example shown in FIG. 6, the distal portion 322d of the clip retention member 302 can be smaller than the proximal portion 322p of the clip retention member 302. Furthermore, the distal and proximal portions 322d, 322p may not be discrete portions, as the strength of the biasing force applied by the clip retention member 302 can gradually change such that it increases from the distal end 302d of the clip retention member 302 towards the proximal end 302p of the clip retention member 302. The distal portion 322d of the clip retention member 302 can be more flexible, softer, or otherwise configured to apply a biasing force with a lesser strength than the proximal portion 322p thereof. The biasing force can change depending on the properties of the clip retention member, such as the clip retention member's elasticity, stiffness, or any other properties. For example, in one embodiment, the clip retention member can have a distal end having a modulus that is less than a modulus of the remainder of the clip retention member. The rigidity or stiffness of the clip retention member can change (e.g., increase) gradually in the proximal direction.

In some embodiments, additionally or alternatively, the clip retention member can be sized and shaped differently along its length. Also, although two clip retention members 302, 304 are described in connection with FIGS. 6, 7, and 8, it should be appreciated that only one of the jaws of a surgical clip applier can include a clip retention member. Furthermore, in some embodiments, more than one clip retention member (e.g., two, three, or more than three) can be formed on or coupled to an inward facing surface of at least one of the jaws of a surgical clip applier. The same or different number of clip retention members can be located on opposed jaws of a surgical clip applier, and the clip retention member can be configured to apply a biasing force to legs of a clip in various manner.

In the embodiment illustrated above in connection with FIGS. 6 to 8, a clip retention member is disposed along a sidewall of a clip guide channel. In some embodiments, at least one clip retention member can be in the form of two clip retention members disposed along upper and lower surfaces of the rails of a clip guide channel. It should be appreciated, however, that the at least one clip retention member can be in the form of a single retention member formed on either surface of the upper and lower surfaces of the clip guide channel.

FIGS. 9A and 9B illustrate an embodiment of a jaw 412 of a surgical clip applier having at least one deflectable clip retention member 402 formed on an inward facing surface 403 of a rail defining the clip track in the jaw 400. As shown in FIG. 9B, the jaw 400 has a clip guide channel 406 that includes an upper rail defining an upper surface 408u of the guide channel 406, a lower rail defining a lower surface 408l of the guide channel, and a sidewall 410 extending between the upper and lower surfaces 408u, 408l. In the illustrated embodiment, the clip retention member 402 can be in the form of a first deflectable clip retention member 402a disposed on the upper surface 408u and a second deflectable clip retention member 402b disposed on the lower surface 408l such that the first and second deflectable clip retention members 402a, 402b engage top and bottom surfaces of a leg of a clip 407 seated therebetween. The clip 407 can be similar to clip 207 in FIG. 5B, or it can be any other clip having first and second legs and configured to be formed when the jaws clamps tissue therebetween.

FIG. 9A illustrates, for the sake of simplicity, one of the clip retention members 402a, 402b, namely the clip retention member 402b. An opposed jaw of the surgical clip applier is not shown in FIGS. 9A and 9B for the sake of brevity, though it should be appreciated that the opposed jaw can have one or more clip retention members similar to the clip retention member 402.

In the embodiment illustrated in FIGS. 9A and 9B, the at least one clip retention member 402 retains the clip 407 by applying a biasing force thereto. The clip 407 can be press-fit or otherwise releasably engaged between the clip retention members 402a, 402b. Each of the clip retention members 402a, 402b is configured to apply a biasing force to the leg of the clip 407 in a direction substantially perpendicular to a plane P1 extending through the jaw 400 and the opposed jaw (not shown). Thus, FIGS. 9A and 9B illustrate schematically that the clip retention members 402a, 402b apply the basing force to the leg of the clip 407 in respective opposed directions substantially perpendicular to the plane P1, as shown by arrows 409a, 409b, respectively. In this way, the leg of the clip 407 is engaged between the clip retention members 402a, 402b. Another leg of the clip 407 can be similarly engaged between clip retention members disposed on the opposed jaw (not shown).

The clip retention members 402a, 402b disposed on the inward facing surface 403 of the jaw 400 can have any suitable configuration. For example, each of them can be in the form of a leaf spring extending longitudinally along the jaw 400, as previously described herein. It should be appreciated, however, that the clip retention members formed on the jaw can have any suitable configurations, including different configurations among the clip retention members. Furthermore, in some embodiments, at least one clip retention member disposed on one jaw of a surgical clip applier can differ from at least one clip retention member disposed on the opposed jaw of the surgical clip applier. The biasing force applied by the clip retention members 402a, 402b can vary along a longitudinal length of the jaw 400, similar to the way a biasing force applied by clip retention member 302 (FIG. 6) can vary. For example, a distal portion of the at least one clip retention member 402 can be more flexible than a proximal portion of the at least one clip retention member 402.

As mentioned above, although two clip retention members 402a, 402b are shown, in some implementations, the at least one clip retention member 402 can be in the form of a single retention member formed on either surface of the upper and lower surfaces of the clip guide channel of the jaw.

In some embodiments, more than one clip retention member can be coupled to a clip track, such as a clip guide channel. The plurality of clip retention members can be coupled to the jaws in various ways, including in different ways along the opposed jaws. The clip retention members can vary in other ways. For example, their overall height can vary along a longitudinal length of the jaw. As another variation, clip retention members having different lengths can be coupled to one or more surfaces of the jaw.

Figure 10:
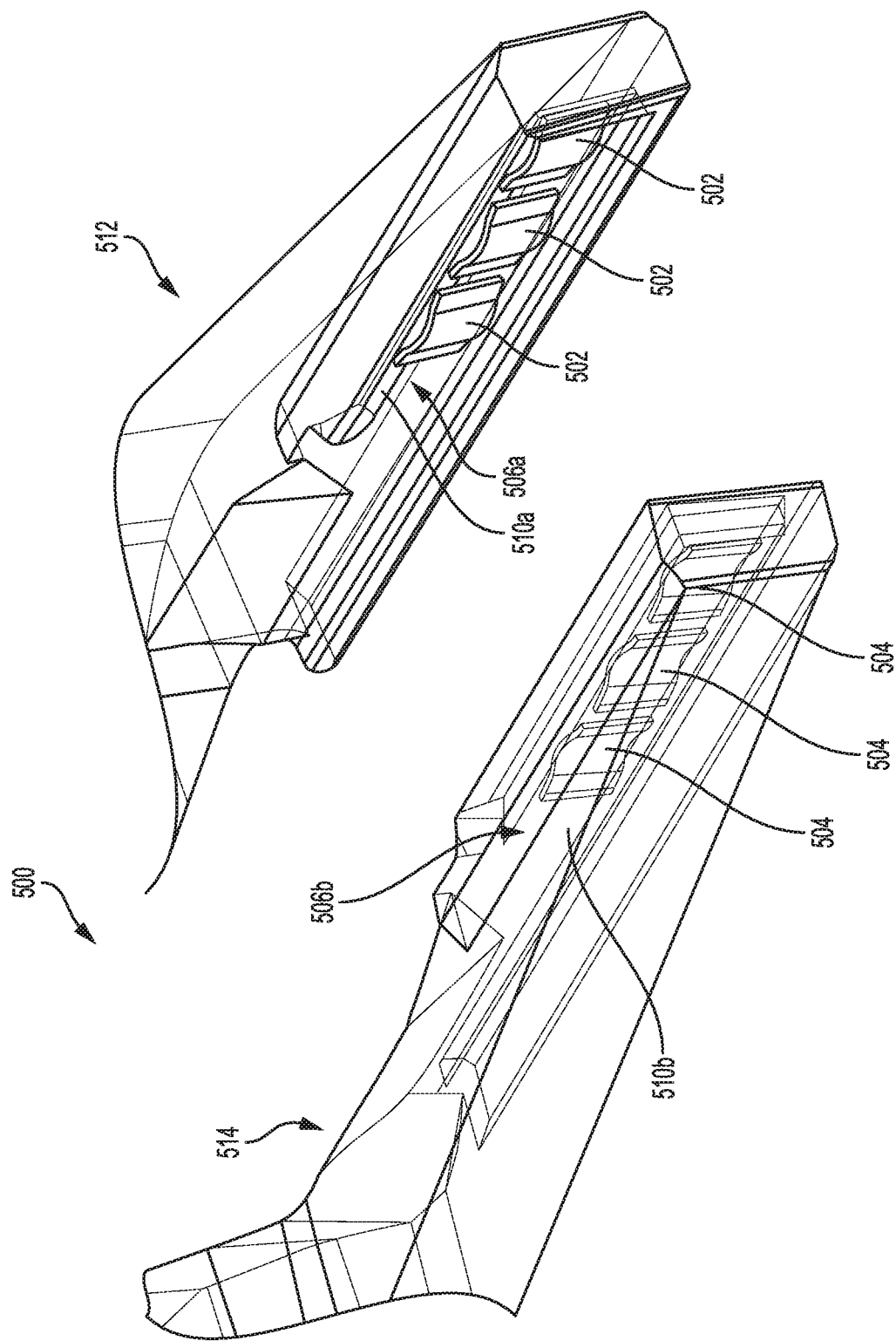
FIG. 10 is a perspective, partially transparent view of another embodiment of jaws of a surgical clip applier having clip retention members on sidewalls of a clip guide channel of each of the jaws.

FIG. 10 illustrates one embodiment of first and second jaws 512, 514 of a surgical clip applier 500 that have multiple clip retention members on inward facing surfaces thereof. In particular, as shown, the first jaw 512 has a plurality of clip retention members 502 coupled to a sidewall 510a of a clip guide channel 506a of the jaw 512. Similarly, the opposed second jaw 514 has a plurality of clip retention members 504 coupled to a sidewall 510b of a clip guide channel 506b of the jaw 514. It should be appreciated that each of the first and second jaws 512, 514 is shown to have three clip retention members 502, 504, respectively, by way of example only. Any suitable number (e.g., two, more than three, etc.) of clip retention members can be disposed on opposed jaws of the surgical clip applier, including different number among the jaws.

Figure 11:
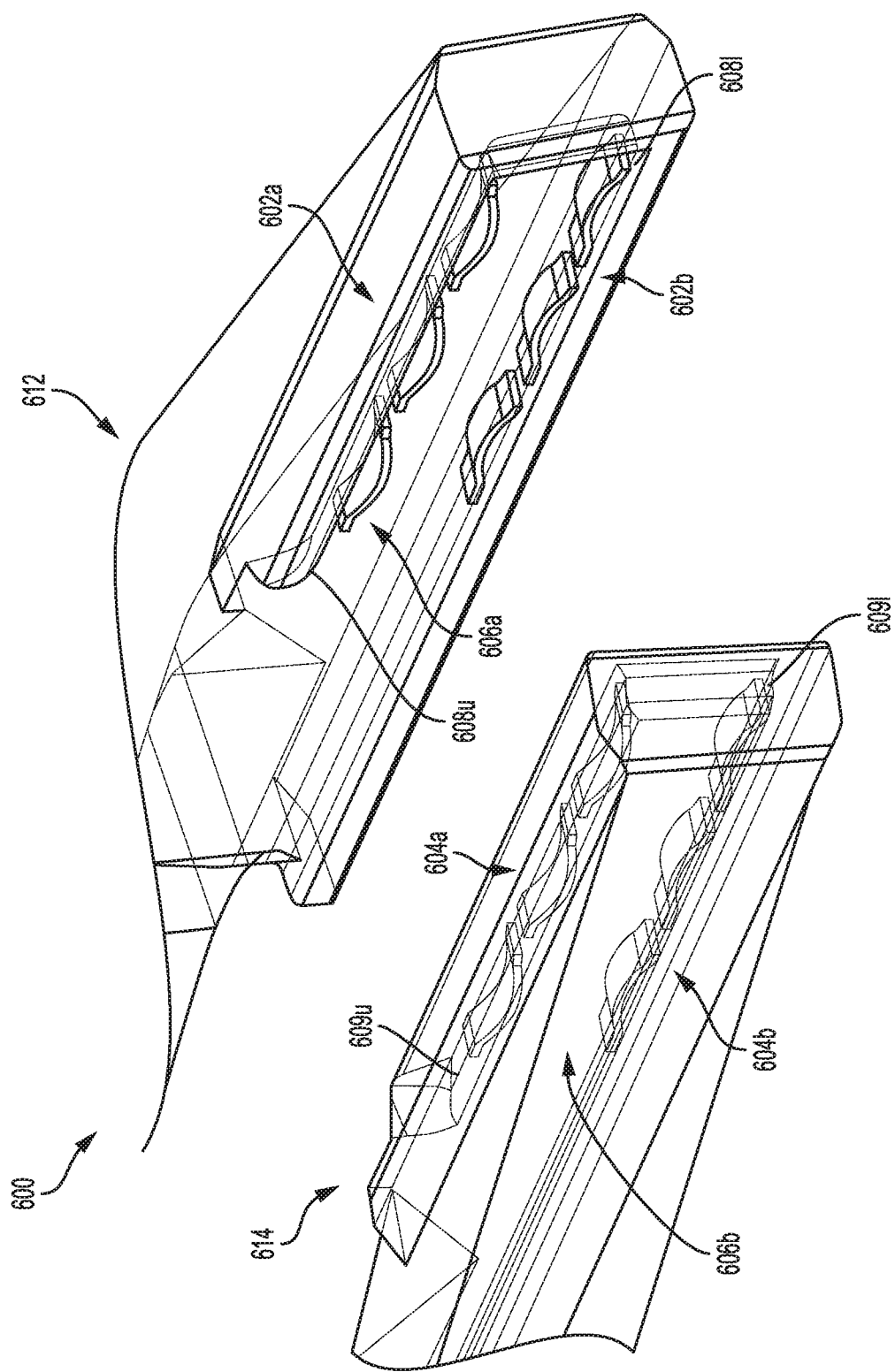
FIG. 11 is a perspective, partially transparent view of jaws of a surgical clip applier according to another embodiment, having clip retention members on upper and lower surfaces of a clip guide channel of each of the jaws.

FIG. 11 illustrates one embodiment of first and second jaws 612, 614 of a surgical clip applier 600 that have multiple clip retention members on inward facing surfaces thereof. In this example, each of the first and second jaws 612, 614 has a plurality of clip retention members on upper and lower walls of the clip guide channel. Thus, as shown, the first jaw 612 has a plurality of clip retention members 602a, 602b coupled to upper and lower surfaces 608u, 608l, respectively, of the upper and lower rails that define a clip guide channel 606a of the jaw 612. Similarly, the second jaw 614 has a plurality of clip retention members 604a, 604b coupled to upper and lower surfaces 609u, 609l, respectively, of the upper and lower rails that define a clip guide channel 606b of the jaw 614. It should be appreciated that each of the first and second jaws 612, 614 is shown to have three clip retention members 602a, 602b and 604a, 604b on the respective upper and lower surfaces of the clip guide channels 606a, 606b by way of example only. Any suitable number (e.g., two, more than three, etc.) of clip retention members can be disposed on the upper and lower surfaces of the clip guide channels of the opposed jaws, including different number among the jaws and different number among the upper and lower surfaces of a clip guide channel of each jaw.

Figure 12:
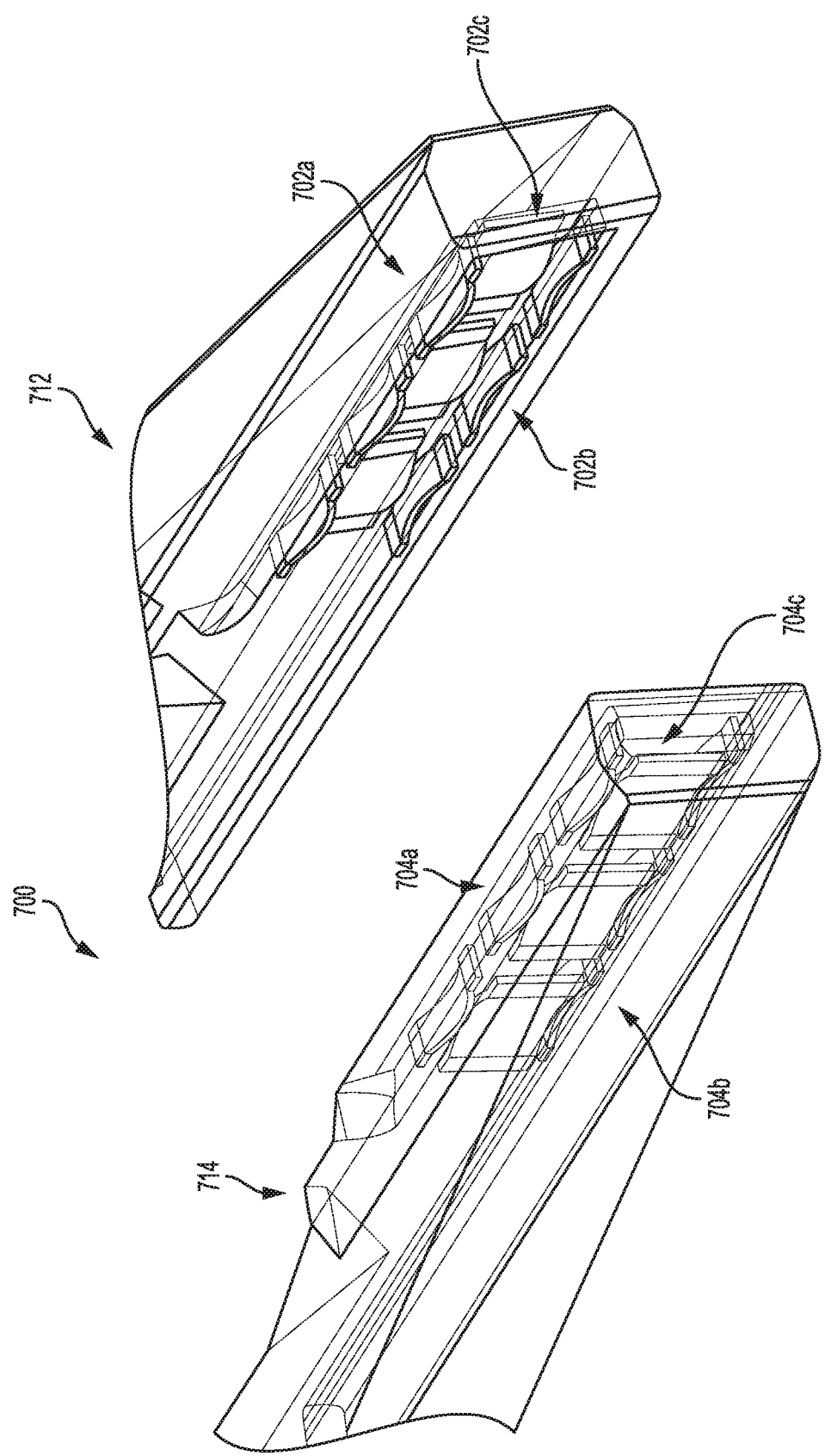
FIG. 12 is a perspective, partially transparent view of jaws of a surgical clip applier having another embodiment of clip retention members on upper and lower surfaces and a sidewall of a clip guide channel of each of the jaws.

FIG. 12 illustrates one embodiment of first and second jaws 712, 714 of a surgical clip applier 700 that have multiple clip retention members on inward facing surfaces thereof. In this example, each of the first and second jaws 712, 714 has a plurality of clip retention members on upper walls, lower walls, and sidewalls of the clip guide channel. Thus, as shown, the first jaw 712 has a plurality of clip retention members 702a, 702b, 702c coupled to the upper surface, lower surface, and the sidewall, respectively, of a clip guide channel of the jaw 712. Similarly, the second jaw 714 has a plurality of clip retention members 704a, 704b, 704c coupled to the upper surface, lower surface, and the sidewall, respectively, of a clip guide channel of the jaw 714. In the illustrated embodiment, the clip retention members 702a, 702b disposed on the upper and lower surfaces of the clip guide channel of the first jaw 712 are aligned with respect to one another and they have a smaller lateral length than the retention members 702c disposed on the sidewall of the clip guide channel of the first jaw 712. The clip retention members 704a, 704b, 704c of the second jaw 714 are similar to clip retention members 702a, 702b, 702c.

It should be appreciated that each of the first and second jaws 712, 714 is shown to have three clip retention members 702a, 702b, 702c, and 704a, 704b, 704c on the respective upper and lower surfaces and sidewalls of the jaw's clip guide channels by way of example only. Any suitable number (e.g., two, more than three, etc.) of clip retention members can be disposed on any of the surfaces of a jaw's clip guide channel.

Figure 13:
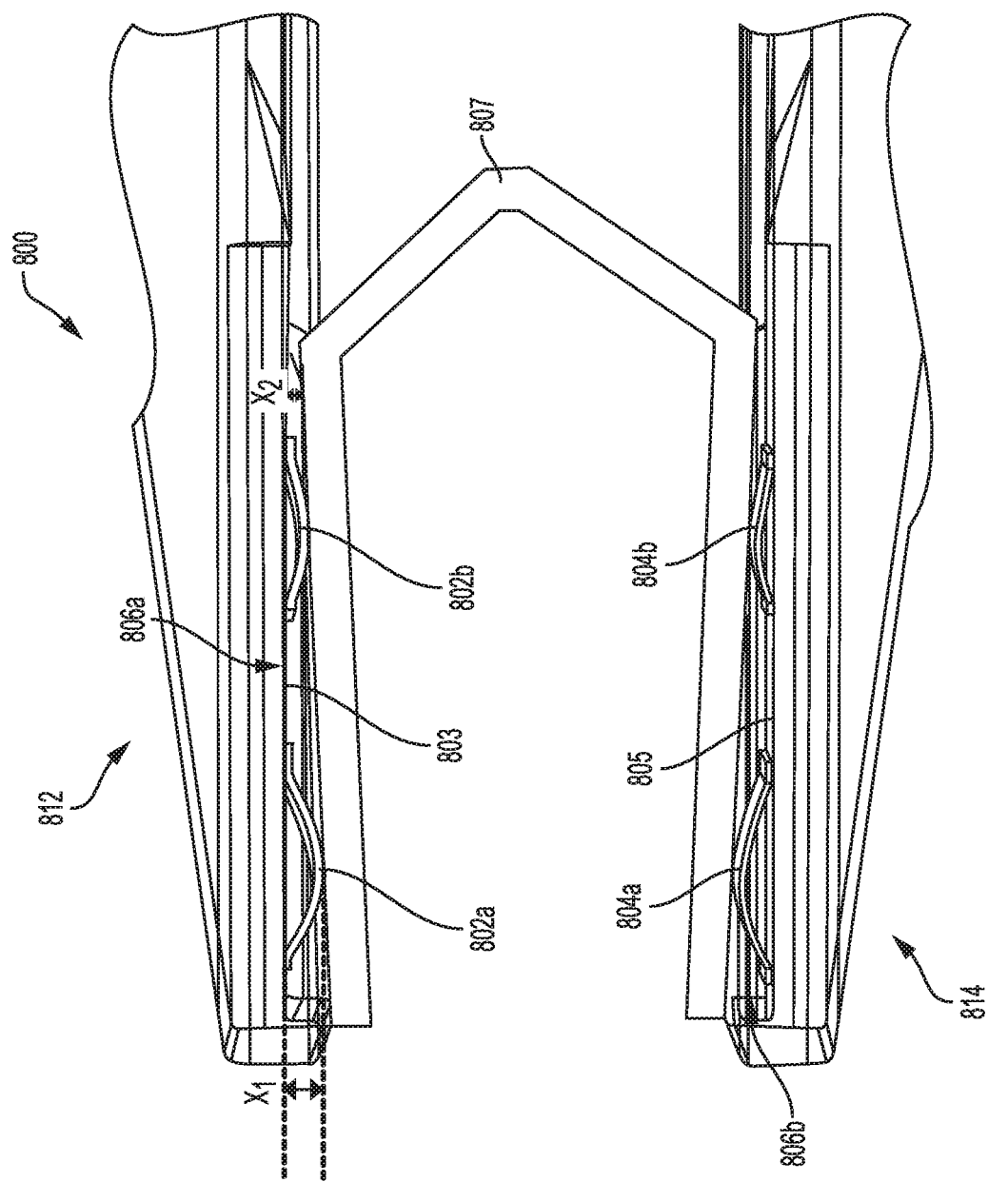
FIG. 13 is a side perspective, partially transparent view of an embodiment of jaws of a surgical clip applier having clip retention members of varying height.

In some embodiments, as mentioned above, a height of the clip retention members can vary along a longitudinal length of jaw. FIG. 13 illustrates one embodiment of first and second jaws 812, 814 of a surgical clip applier 800 that have clip retention members on inward facing surfaces thereof 803, 805, where each of the jaws has clip retention members of different heights. In particular, as shown in FIG. 13, the first jaw 812 has first and second clip retention members 802a, 802b disposed on an upper surface of a clip guide channel 806a, where the first clip retention member 802a has a first height X1 while the second clip retention member 802a has a second height X2. The first height X1 is greater than the second height X2, to compensate for an inward tapered configuration of a clip 807 when the clip 807 is disposed between the jaws 812, 814.

In the example of FIG. 13, each of the clip retention members 802a, 802b has a generally curved shape and its height is measured as a distance between a top of the curve and the respective inward facing surface of the jaw. The clip retention members can have various other configurations, and their height can be defined as a distance between a point on the clip retention member that is farthest from the inward facing surface of the jaw on which the clip retention member is disposed. In the example illustrated in FIG. 13, a length of the first clip retention member 802a is greater than a length of the second clip retention member 802b, and the clip retention members 802a, 802b are disposed at a distance from one another. It should be appreciated that the inward facing surface 803 of the jaw 812 can have more than two clip retention members that can be disposed at any suitable distance from one another. A clip guide channel 806b on the inward facing surface 805 of the jaw 814 has first and second clip retention members 804a, 804b that can be configured similarly to the clip retention members 802a, 802b.

Opposed jaws of a surgical clip applier can have a plurality clip retention members that are positioned in various ways along inward facing surfaces of the jaws. FIGS. 14A and 14B illustrate one embodiment of first and second jaws 912, 914 of a surgical clip applier 900 that have clip retention members that are staggered along the inward facing surfaces of each jaw, and are also staggered with respect to the opposed jaw. Thus, the first jaw 912 has first clip retention members 902a on an upper surface 908u of a clip guide channel 906a thereof that are staggered with respect to second clip retention members 902b on a lower surface 908l of the clip guide channel 906a. The second jaw 914 has third clip retention members 904a on an upper surface 909u of a clip guide channel 906b thereof that are staggered with respect to fourth clip retention members 904b on a lower surface 909l of the clip guide channel 906b. Also, the first and second clip retention members 902a, 902b of the first jaw 912 can be staggered with respect to the third and fourth clip retention members 904a, 904b of the second jaw 914. It should be appreciated that each of the jaws 912, 914 is shown to have three clip retention members on the upper and lower surfaces of the jaw's clip guide channel by way of example only, as the jaws can have any suitable number of clip retention members. Also, although the clip retention members 902a, 902b and 904a, 904b are in the form of inwardly curved members, the clip retention members can have any other suitable shapes and they can be disposed at various distances from one another.

Figure 14C:
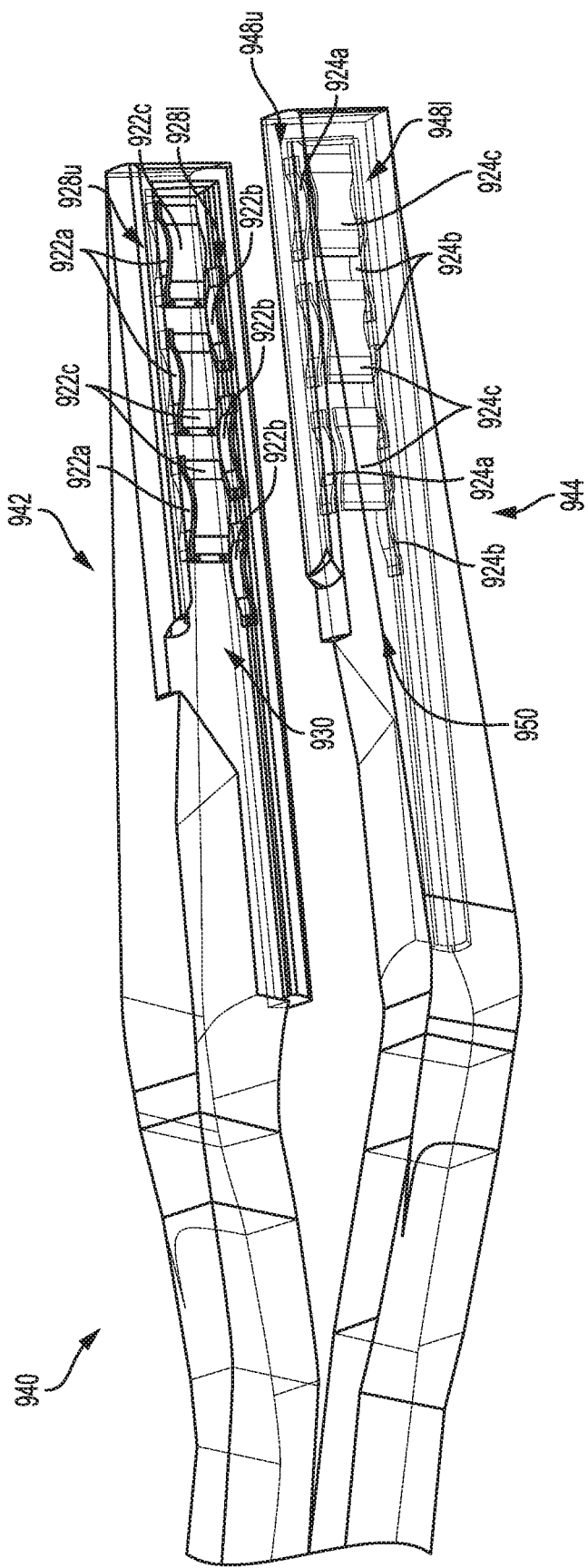
FIG. 14C is a perspective, partially transparent view of an embodiment of jaws of a surgical clip applier having staggered clip retention members on upper and lower surfaces of a clip guide channel of each of the jaws, as well as clip retention members on a sidewall of the clip guide channel of each of the jaws.

FIG. 14C illustrates an embodiment of first and second jaws 942, 944 of a surgical clip applier 940. In this example, each of the first and second jaws 942, 944 has clip retention members formed on an upper surface, a lower surface, and a sidewall of a jaw's clip guide channel, and the clip retention members are similar to those shown in FIG. 12. As shown in FIG. 14C, the first jaw 942 has first, second, and third clip retention members 922a, 922b, 922c formed on the jaw's upper surface 928u, lower surface 928l, and a sidewall 930 extending between the upper and lower surfaces 928u, 928l. As shown, the first and second clip retention members 922a, 922b are staggered with respect to each other, and the first and third clip retention members 922a, 922c are aligned with respect to each other. Similarly, as shown in FIG. 14C, the second jaw 944 has fourth, fifth, and sixth clip retention members 924a, 924b, 924c formed on the jaw's upper surface 948u, lower surface 948l, and a sidewall 950 extending between the upper and lower surfaces 948u, 948l. In this example, the fourth and fifth clip retention members 924a, 924b are staggered with respect to each other, and the fourth and sixth clip retention members 924a, 924c are aligned with respect to each other. It should be appreciated that nine clip retention members are shown on each of the jaws 942, 944 by way of example only, as the jaws can have any suitable number of clip retention members, including a different number of clip retention members among the different surfaces of a clip guide channel of the same jaw, and a different number of clip retention members among the jaws.

The clip retention members described above can be in the form of leaf springs or other suitable elements. The clip retention member in accordance with the described embodiments can be made from any suitable material. For example, it can be made from metal, plastic, or any suitable combination of materials such that the clip retention member is resiliently deformable. The clip retention member can be elastically deformable. In some embodiments, as discussed above, a biasing force applied by the clip retention member on a clip leg can vary. In this way, elasticity of the clip retention member can vary along its length. The clip retention member can be coupled to a respective inward facing surface of the jaw in any suitable manner, e.g., welded, glued, attached using a suitable mechanism, etc. In some embodiments, the clip retention member can be integrally and/or monolithically formed with the corresponding inward facing surface of the jaw. As mentioned above, the clip retention member can be coupled to the inward facing surface at one or more portions of the clip retention member.

Retention of a clip by jaws of a surgical clip applier can be improved in other various ways. For example, a jaw of a surgical clip applier can have other features that facilitate retention of a clip by the jaw and proper positioning of a clip prior to its passage through tissue and formation. The jaw can have one or more features that prevent the clip from backing up proximally once the clip is advanced to be seated between the jaws. Such feature(s) can be tabs, protrusions, or any other types of features that facilitate clip's resistance to proximal pressure exerted thereon by the jaws. The feature can be disposed on the jaw such that the feature has a fixed configuration. Alternatively, the feature can be deflectable such that it can be flush with or align with the surface of the jaw as the clip is advanced distally between the jaws, and the feature can defect once the clip moves distally past the feature.

For example, in some embodiments, a clip track of a jaw of a surgical clip applier can include at least one deflectable tab configured to engage a proximal surface of a clip after the clip moves distally past the at least one deflectable tab. Thus, the at least one deflectable tab in the clip track prevents proximal movement of the clip within the clip track. FIG. 15 shows one embodiment of jaws 1012, 1014 of a surgical clip applier 1000 that have deflectable tabs 1020, 1022 included in clips tracks 1006a, 1006b defined in inward facing surfaces of the jaws 1012, 1014, respectively. The tabs 1020, 1022 are configured to engage a proximal surface 1007p of a clip 1007 after the clip moves distally past the deflectable tab 1020, 1022, as shown in FIG. 15. The tabs 1020, 1022 are configured to defect towards distal ends 1012d, 1014d of the jaws 1012, 1014. The tabs 1020, 1022 are formed such that they engage areas of legs 1007a, 1007b of the clip 1007 that are proximal to respective knees 1009a, 1009b of the legs 1007a, 1007b. The tabs 1020, 1022 can be formed on the jaws 1012, 1014 in any suitable manner. For example, the tabs 1020, 1022 can be coupled to the jaws or they can be integrally formed with the jaws 1012, 1014. The tabs 1020, 1022 are shown in FIG. 15 by way of example only, as any other features can be disposed on jaws a clip applier to prevent proximal movement of a clip within clip tracks of the jaws.

It should be appreciated that tabs similar to the tabs 1020, 1022, or tabs having any other configuration, can be formed on the opposed jaws in conjunction with clip retention members. Thus, although FIG. 15 does not show clip retention members, the jaws 1012, 1014 can have clip retention members disposed thereon, such as any of the clip retention members described herein. Also, any of the clip retention members described herein can be disposed on a jaw of a clip applier in association with one or more deflectable tab configured to engage a proximal surface of a clip after the clip moves distally past the deflectable tab(s).

In some embodiments, a clip track defined in an inward facing surface of at least one of the jaws is in the form of a groove or channel formed in the jaw. Such a clip track can be formed within the surface of the jaw by stamping or using any other suitable technique. In other embodiments, however, a clip track can be a separate component that is attached to the jaw using a suitable technique. In such embodiments, the clip track can serve as a clip retention member. For example, at least a portion of the clip track coupled to a jaw, such as a portion facing the opposed jaw, can be configured to deflect or deform to conform to a shape of a leg of a clip when the clip is disposed between the jaws. Manufacturing costs and complexity can be reduced to make a jaw having a separate clip track coupled thereto.

Figure 16:
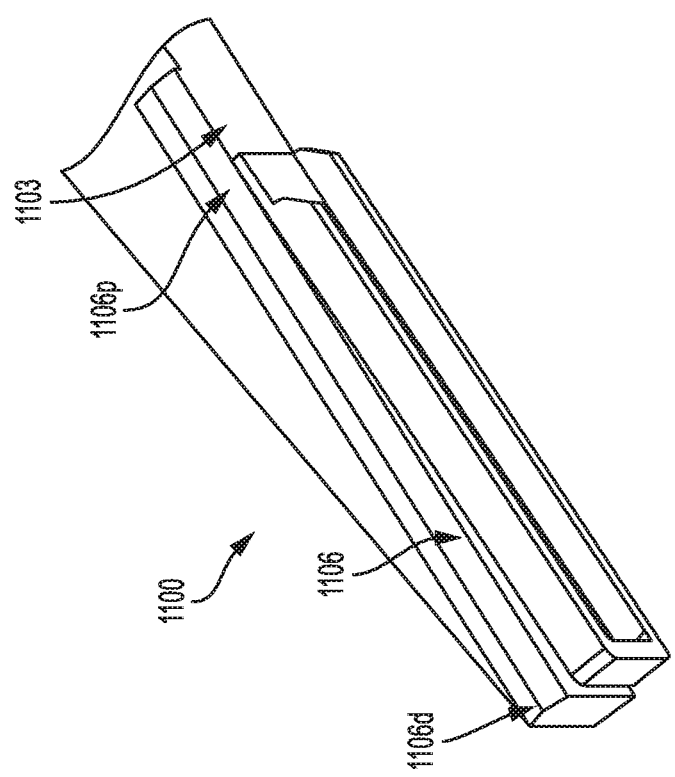
FIG. 16 is a perspective view of an embodiment of a jaw of a surgical clip applier having a separate clip track coupled thereto.

FIG. 16 illustrates a jaw 1100 of a surgical clip applier having a clip track 1106 coupled to an inward facing surface 1103 thereof. The clip track 1106 is a separate component attached to the jaw 1100 in a suitable manner, for example, by welding, applying adhesive (e.g., an ultraviolet (UV) curable adhesive), or using an attachment mechanism (e.g., a pin, rivet, screw, etc.). In this example, the clip track 1106 has a generally rectangular longitudinal cross-section and it is disposed along a length of the inward facing surface 1103, as shown in FIG. 16. The clip track 1106 is configured to apply a biasing force to a leg of a clip a direction substantially perpendicular to a plane extending through the jaw 1100 and the opposed jaw (not shown). However, in some implementations, the clip track 1106 is configured to apply a biasing force to a leg of a clip a direction of the plane extending through the jaw 1100 and its opposed jaw of the surgical clip applier. Moreover, the clip track can be configured such that it can apply a biasing force in more than one direction. Furthermore, although the clip track 1106 is shown without any additional clip retention members, in some embodiments, the clip track 1106 can have one or more clip retention members coupled thereto.

The clip track 1106 can be made from a suitable metal, or any other suitable material or a combination of materials. In some embodiments, a thickness of the clip track walls can be in the range of from about 0.003 inches to about 0.030 inches. The thickness of the clip track can be substantially the same along its length. In some embodiments, the thickness of the clip track can vary along its length—for example, it can decrease from the clip track's distal end 1106d towards its proximal end 1106p.

Figure 17:
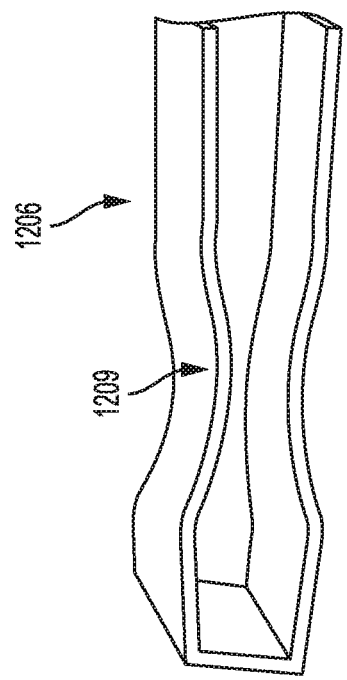
FIG. 17 is a perspective schematic view showing an embodiment of a separate clip track.

A clip track formed separately and attached to a jaw, such as the clip track 1106 in FIG. 16, or any other clip track, can be at least partially deformable, which can be done in a number of different ways. For example, the clip track can be made (e.g., stamped) from a suitable metal and it can have deformable elements (e.g., springs or other deformable elements) stamped or otherwise introduced onto one or more of surfaces of the clip track. FIG. 17 shows an example of a pre-formed clip track 1206. To show that the clip track 1206 is deformable, FIG. 17 illustrates schematically (arrow 1209) that, when manufactured, the walls of the clip track purposely have a partially concave shape, such that they would provide resistive compressive pressure to a clip, once the clip is advanced into these clip track walls, thus straightening the concave shape. The clip track 1206 can have one or more deformable elements (not shown) stamped or otherwise introduced onto one or more of its surfaces.

In some embodiments, a clip track can have deformable elements disposed on one or more surfaces thereof. The clip track can be molded (e.g., metal injection molded), and it can deflect or deform to conform to a shape of a leg of a clip. FIG. 18 illustrates an embodiment of a jaw 1300 of a surgical clip applier having a clip track 1306 coupled thereto that has a deformable tab 1316. The tab 1316 can be coupled to the clip track 1306 in a suitable manner. In the illustrated embodiment, the tab 1316 extends along a longitudinal length of the clip track 1306 on an inward facing surface 1307 of the clip track 1306 at a proximal end 1306p of the clip track 1306, such as at location 1311.

FIGS. 19A and 19B illustrate another embodiment of a jaw 1400 of a surgical clip applier having a clip track 1406 coupled thereto that has a deformable tab 1416. In this example illustrated, the tab 1416 is formed on an inward facing surface 1411 of the clip track 1406 adjacent to a proximal end 1406p of the clip track 1406. The tab 1416 is relatively small such that it extends along a portion of a longitudinal length of the clip track 1406.

It should be appreciated that the tab 1316 (FIG. 18) and tab 1416 (FIGS. 19A and 19B) can be disposed at any suitable locations on the respective clip tracks. Also, one or more of these tabs can be similar to tabs 1020, 1022 in FIG. 15. Each tab can be coupled to the clip track in any a suitable manner. For example, the tab can be molded into the surface of the clip track. Furthermore, in some embodiments, the tab can be integrally formed with the clip track. Also, more than one tabs or other clip retaining feature can be formed on the clip track. Regardless of its specific configuration, size, and position relative to the clip track, at least one tab is configured to assist in proper retention of a leg of a clip by the jaw to which the clip track is attached.

A clip retention member can have many various forms. For example, in some embodiments, a clip retention member can be in the form of an elongate member coupled to a clip guide channel and having a plurality of deflectable extensions. The extensions, such as, for example, multiple flexible fingers are configured to provide compliant support to guide a clip and maintain proper position of the clip. FIGS. 20-22 illustrate examples of clip retention members having a plurality of deflectable extensions. FIG. 20 shows a jaw 1500 of a surgical clip applier having a clip guide channel 1506 that has a clip retention member 1502. As shown, the clip retention member 1502, which can be disposed on a sidewall of the clip guide channel 1506, has a plurality of deflectable extensions 1511 extending along a longitudinal length of the clip retention member 1502 between proximal and distal ends 1502p, 1502d of the clip retention member 1502. The deflectable extensions 1511 can be, for example, fingers or other features that can be coupled to a body 1509 of the clip retention member 1502 by insert molding, using an adhesive (e.g., a UV-activated adhesive), or in any other suitable manner. Alternatively, in some embodiments, the extensions 1511 can be integrally formed with the body 1509 of the clip retention member 1502. The deflectable extensions 1511 can have any suitable length. Also, in some embodiments, as in the example illustrated in FIG. 20, the extensions 1511 are biased in a direction of a movement of a clip—towards a distal end 1500d of the jaw 1500.

FIG. 21 illustrates a jaw 1600 of a surgical clip applier having a clip guide channel 1606 that has a clip retention member 1602. As shown, the clip retention member 1602, which can be disposed on a sidewall of the clip guide channel 1606, has a plurality of deflectable extensions 1611 extending along a longitudinal length of the clip retention member 1602 between proximal and distal ends 1602p, 1602d of the clip retention member 1602. In this example, length of the deflectable extensions 1611 varies along the longitudinal length of the clip retention member 1602. In particular, as shown in FIG. 21, the length of the extensions 1611 increases from the proximal end 1602p of the clip retention member 1602 towards the distal end 1602d of the clip retention member 1602. Similar to extensions 1511 (FIG. 20), the extensions 1611 can be biased towards a distal end 1600d of the jaw 1600, in a direction of a movement of a clip when the clip is positioned between the jaw 1600 and an opposed jaw (not shown).

At least one clip retention member having deflectable extensions can be disposed on one or more of upper and lower surfaces, and a sidewall of a clip guide channel of a jaw. FIG. 22 illustrates an example of a jaw 1700 of a surgical clip applier having a clip retention member 1702 with a plurality of deflectable extensions 1711 disposed on an upper surface 1708u of a clip guide channel 1706 of an inward facing surface of the jaw 1700.

Deflectable extensions shown in FIGS. 20-22, or other deflectable extensions in accordance with the described techniques, can be formed from any suitable material(s). For example, they can be formed from a suitable plastic. The deflectable extensions can be made from elastomeric material.

In some embodiments, the deformable clip retention members are not separate from the clip guide rail surfaces, but are instead in the form of upper and lower jaw rails angled inward, such that a slight interference fit is generated between the jaws and clip's legs, and the clip's legs are biased to bottom out on side walls of the jaw guide rail. Thus, in some embodiments, that are discussed in more detail below, jaws of a surgical clip applier and a surgical clip can tapered in axial and transverse directions, in various ways, such that no additional biasing elements (e.g., springs) is required.

Figure 23A:
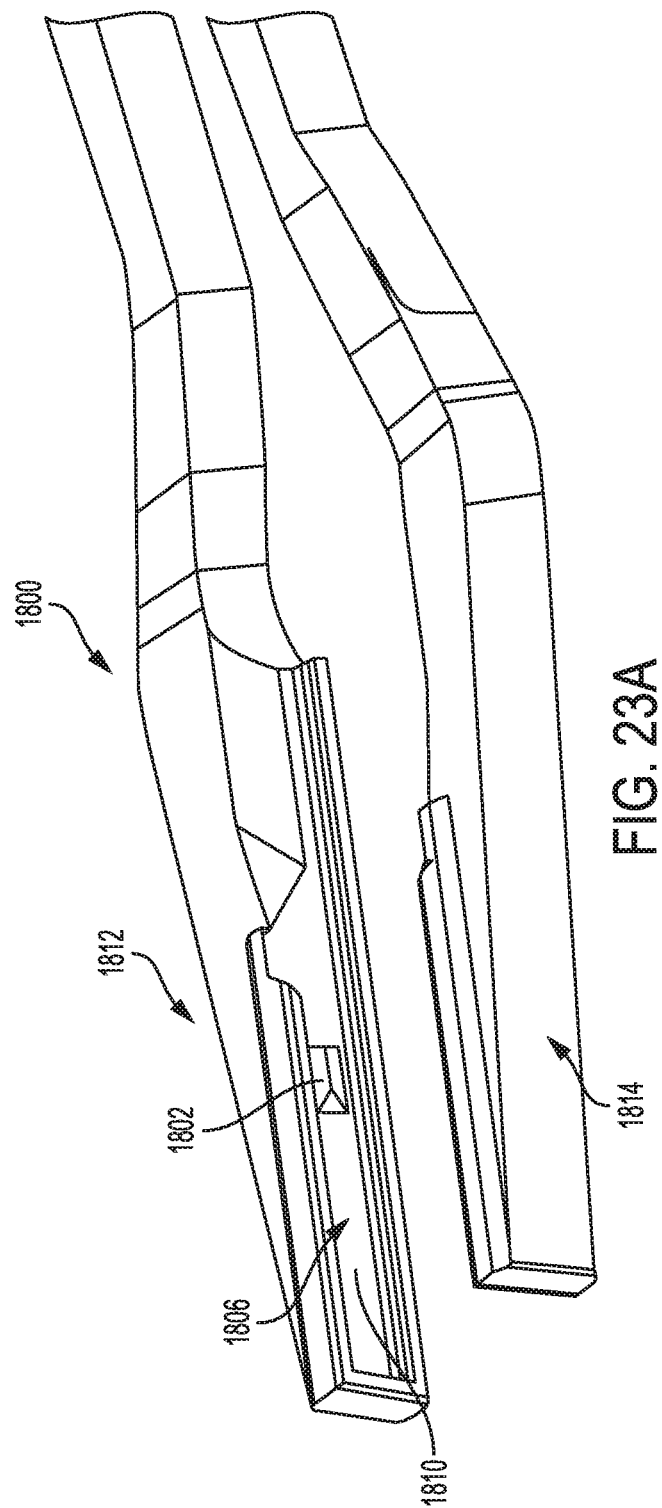
FIG. 23A is a perspective view of a portion of jaws of a surgical clip applier having at least one mating feature configured to mate with a surgical clip, according to another embodiment.
Figure 23B:
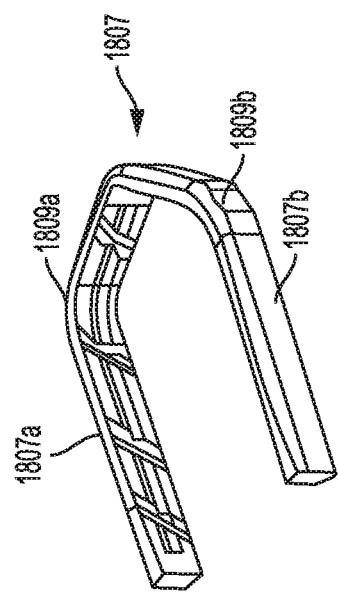
FIG. 23B is perspective view of an embodiment of a surgical clip.

In some embodiments, clip retention by one or both jaws of a surgical clip applier can be facilitated by releasably engaging the clip with at least one of the jaws using mating features of the jaws and/or the clip. Accordingly, in some embodiments, a jaw of a surgical clip applier can have one or more mating features in a clip guide channel configured to engage a portion of a surgical clip when the clip is positioned between jaws of the clip applier. For example, a mating feature, such as a recess, can be formed in a jaw's clip guide channel at a location in the clip guide channel where a clip knee is disposed. Thus, the knee of the clip can be mated with the recess, which can facilitate clip retention during forming of the clip. FIG. 23A illustrates an embodiment of first and second jaws 1812, 1814 of a surgical clip applier 1800, where at least the first jaw 1812 has a mating feature in the form of a recess 1802 in a sidewall 1810 of a clip guide channel 1806 of the jaw 1812. The recess 1802 is formed in the sidewall 1810 at a location that corresponds to a location of a knee 1809*a* of a first leg 1807*a* of a surgical clip 1807 shown in FIG. 23B. In this way, the knee 1809 of the clip 1807 can be received within the recess 1802 when the clip 1807 is advanced into between the jaws 1812, 1814. Although obscured in FIG. 23A, the second jaw 1814 also has a similar mating feature formed therein and configured to receive a knee 1809*b* of a second leg 1807*b* of the clip 1807.

Figure 23E:
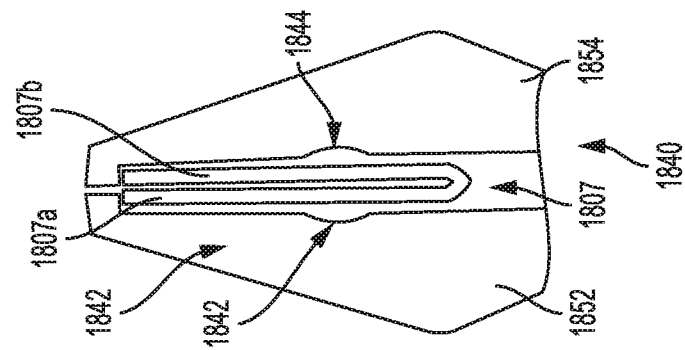
FIG. 23E is another cross-sectional top view of the jaws of FIG. 23D, showing the clip disposed between the jaws and fully formed.
Figure 23D:
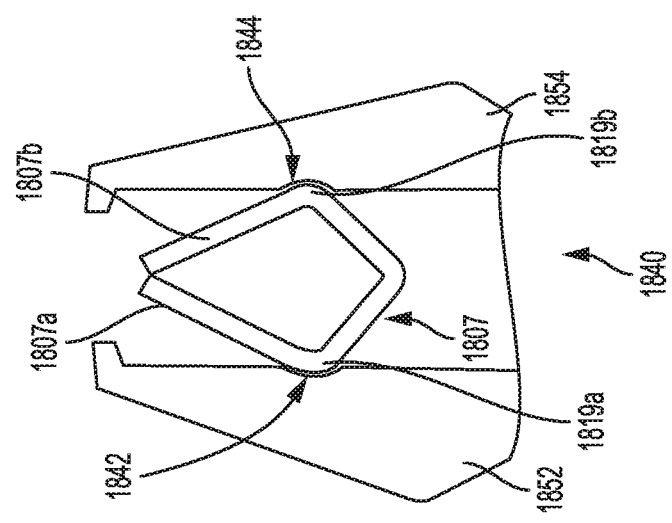
FIG. 23D is a cross-sectional top view of the jaws of FIG. 23C, showing the clip disposed between the jaws and in a partially closed position.
Figure 23C:
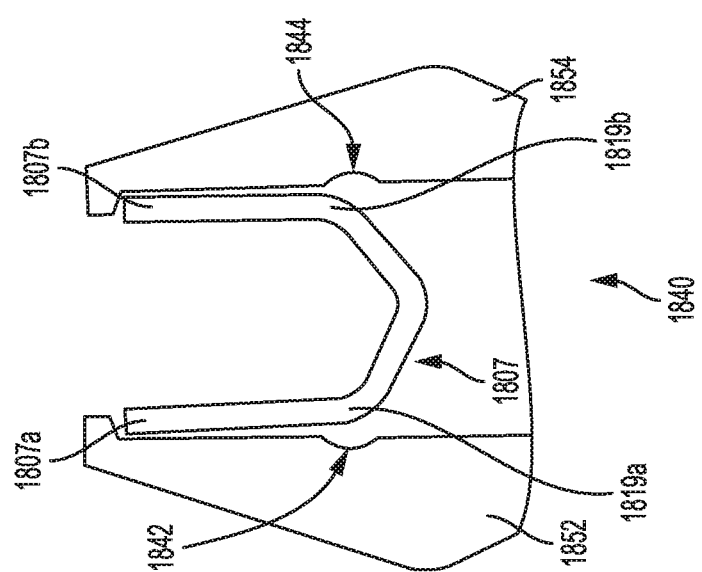
FIG. 23C is a cross-sectional top view of an embodiment of jaws of a surgical clip applier having recesses configured to mate with a surgical clip, showing the clip disposed between the jaws in an initial stage of clip formation.

FIGS. 23C-23E additionally illustrate one embodiment of first and second jaws 1852, 1854 of a surgical clip applier 1840, where each of the jaws 1852, 1854 has a respective mating feature in the form of recesses 1842, 1844 in a sidewall of a clip guide channel of the jaws. The recesses 1842, 1844 can have any suitable shapes and, in the illustrated embodiments, they are shaped and sized to fit knees of the clip. The first and second jaws 1852, 1854 can be similar to the jaws 1812, 1814 of FIG. 23A. Thus, the recesses 1842, 1844 are formed in the sidewall of each of the jaws at a location that corresponds to a location of a knee 1819*a* of a first leg 1807*a* of a surgical clip 1807 and a knee 1819*b* of a second leg 1807*b* of the surgical clip 1807. FIG. 23C shows the clip 1807 disposed between the jaws 1852, 1854 when it has been initially advanced between the jaws in an unformed configuration. FIG. 23D shows that, during an intermediate phase of formation of the clip 1807 (prior to fully forming the clip), distal tips of the clip's legs 1807*a*, 1807*b* are brought together, such that the clip 1807 becomes diamond-shaped. The recesses 1852, 1854 generate additional support for the clip knees 1819*a*, 1819*b*, thus resisting any tilting or dislodgement of the clip 1807 during this intermediate phase of clip formation. FIG. 23E shows the clip 1807 disposed between the jaws in the fully formed configuration.

It should be appreciated that one recess 1802 in FIGS. 23A and 23C-23E is shown by way of example only, as any other number (e.g., two, more than two, etc.) of recesses or other types of mating features can be formed on the inward facing surface of the jaw. The at least one recess can have any suitable shape, for example, in the illustrated embodiment, the recess that conform to the shape of the clip's knee. However, it should be appreciated that the recess can have any other suitable shape—e.g., it can have a generally rectangular, oval, elongated, or any other cross-section, and it can be configured to engage with a portion of a clip rather than a clip's knee. Regardless of its specific configuration, the recess, or other mating feature configured to mate with a portion of the clip, is configured such that it releasably engages with clip moved between the jaws and thus facilitates retention of the clip by the jaw(s) prior to and during clip formation.

Figure 24A:
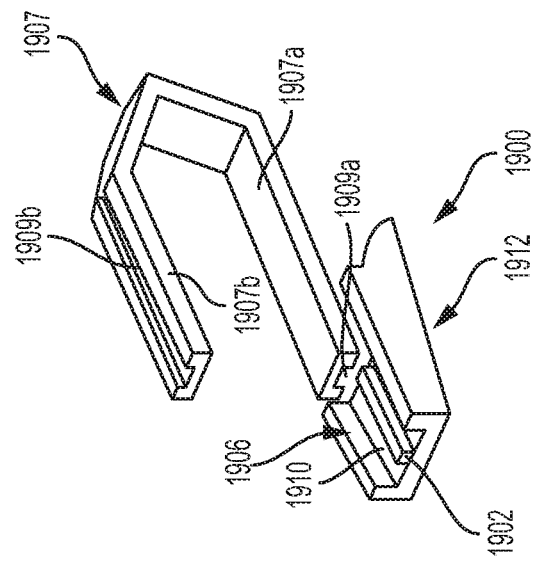
FIG. 24A is a cross-sectional, partially transparent perspective view of an embodiment of a surgical clip applier having a male mating feature configured to mate with a corresponding female mating feature of a surgical clip.
Figure 24B:
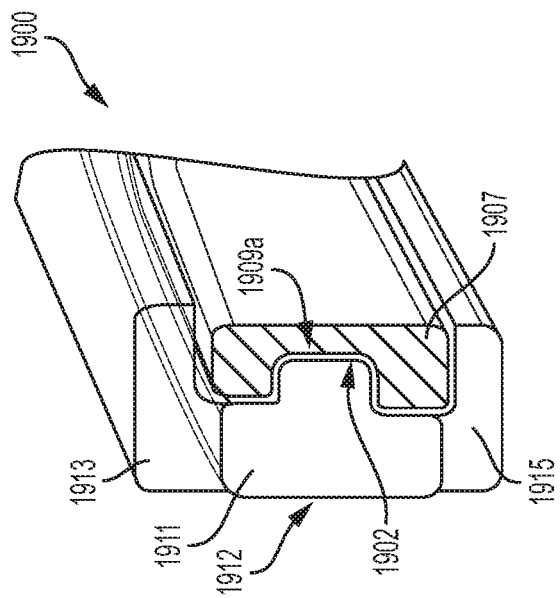
FIG. 24B is a perspective view of a portion of the jaw of FIG. 24B showing a surgical clip seated therein.

In some embodiments, one or both jaws of a surgical clip applier can have at least one mating feature in a clip guide channel configured to releasably engage at least one corresponding mating feature of a surgical clip when clip when the clip is positioned between jaws of the clip applier. FIGS. 24A and 24B illustrate an embodiment of a first jaw 1912 of a surgical clip applier 1900, where the jaw 1912 has at least one male mating feature configured to mate with at least one corresponding female mating feature formed on a surgical clip 1907. As shown, the first jaw 1912, which is representative of both jaws of the surgical clip applier 1900, has a mating feature 1902 in the form of a longitudinal protrusion formed in a sidewall 1910 of a clip guide channel 1906 of the jaw 1912. The clip 1907 has a corresponding longitudinal groove or recess 1909*a* formed on a first leg 1907*a* thereof. As shown in FIG. 24B, a second leg 1907*b* of the clip also has a longitudinal recess 1909*b* configured to mate with a protrusion of the jaw opposed to the jaw 1912. As shown in FIG. 24A, when the clip 1907 is disposed between the jaws of the surgical clip applier 1900, the longitudinal protrusion 1902 of the jaw 1912 releasably mates with the recess 1909*a* formed in the clip 1907. In this example, as shown in FIG. 24B, the recess 1909*a* is formed along the entire length of a portion the clip's leg 1907*a* that mates with the jaw during the clip formation. A length of the longitudinal protrusion 1902 of the jaw 1912 can correspond to a length of the recess 1909*a* of the clip 1907, though it can have any suitable length.

As shown in FIG. 24A, the clip 1907 mates with the jaw 1912 such that the clip 1907 is enclosed by upper and lower rails 1913, 1915 of the jaw 1912 having the sidewall 1910 (marked in FIG. 24B) extending therebetween. In at least some embodiments, the upper and lower rails 1913, 1915 can be removably coupled to the jaw 1912. For example, the upper and lower rails 1913, 1915 can be configured to frictionally engage with respective opposed sides of a jaw's body 1911. However, the upper and lower rails 1913, 1915 can be configured to be removably coupled to the jaw 1912 in other suitable ways.

The recesses 1909*a*, 1909*b* of the clip 1907 can vary in many different ways. For example, although the recesses 1909*a*, 1909*b* are shown as having a generally rectangular cross-section, they can have any other shapes. Similarly, the protrusions of the jaws, such as the protrusion 1902, can have a rectangular cross-section, as in the illustrated embodiment, or the protrusion formed on each of the jaws can have other configurations in other embodiments. Also, although one recess in a clip is shown to mate with a protrusion of a jaw, in some embodiments, more than one recess can be formed on the clip's legs and the jaw will thus have more than one corresponding protrusions.

Figure 24C:
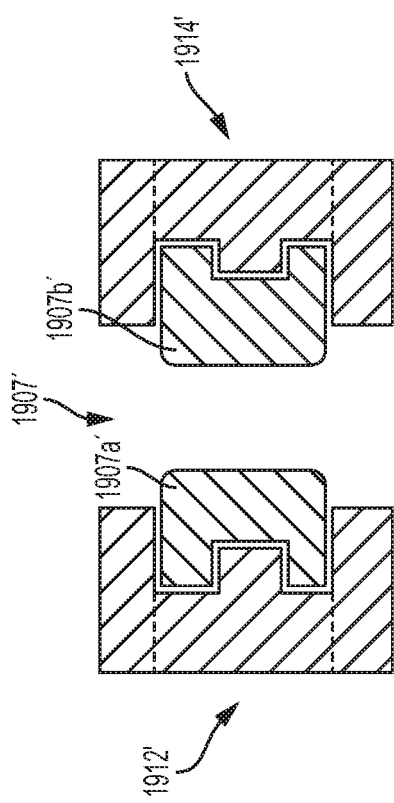
FIG. 24C is a lateral cross-sectional view of an embodiment of jaws of a surgical clip applier each having a male mating feature configured to mate with a corresponding female mating feature of a surgical clip.

FIG. 24C shows another example of first and second jaws 1912', 1914' of a surgical clip applier that is similar to the clip applier 1900 of FIGS. 24A and 24B. As shown in FIG. 24C, each of the first and second jaws 1912', 1914' has a respective protrusion configured to mate with a corresponding recess in first and second legs 1907a', 1907b' of a surgical clip 1907'.

Figure 24D:
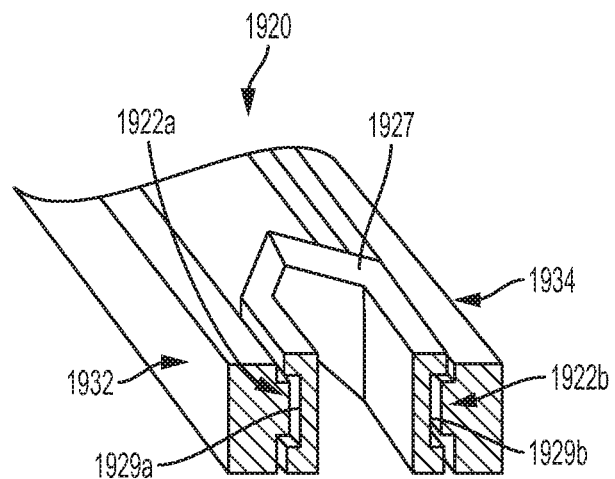
FIG. 24D is a perspective view of an embodiment of jaws of a surgical clip applier each having a male mating feature configured to mate with a corresponding female mating feature of a surgical clip.

FIG. 24D illustrates an embodiment of first and second jaws 1932, 1934 of a surgical clip applier 1920 that is similar to surgical clip applier 1900 in FIGS. 24A and 26B and is therefore not described in detail. As shown in FIG. 24D, the jaws 1932, 1934 have corresponding longitudinal protrusions 1922a, 1922b on sidewalls thereof that are configured to mate with respective recesses 1929a, 1929b formed in first and second legs of a clip 1927. In this example, the first and second jaws 1932, 1934 are shown without upper and lower rails. As mentioned above, the rails can be removable. Thus, although the jaws 1932, 1934 are shown in FIG. 24D without the rails, the jaws 1932, 1934 can be configured to removably mate with suitable upper and lower rails. However, in some embodiments, the clip applier 1920 is configured to operate with its jaws not having the upper and lower rails.

Figure 24E:
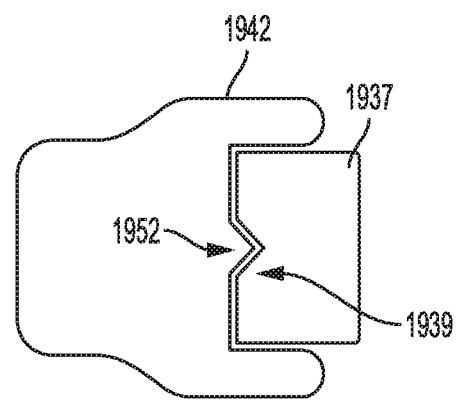
FIG. 24E is a side view of an embodiment of a jaw of a surgical clip applier having a male mating feature configured to mate with a corresponding female mating feature of a surgical clip.

As mentioned above, the mating features of a surgical clip and the corresponding (e.g., complementary) mating features of a jaw can have various configurations. FIG. 24E shows one embodiment of a jaw 1942 of a surgical clip applier having a male mating feature 1952 in the form of a longitudinal protrusion having a triangular cross-section. As shown, the male mating feature 1952 is configured to mate with a corresponding longitudinal recess 1939 in a surgical clip 1937, the recess 1939 also having a triangular cross-section.

In some embodiments, jaws of a surgical clip applier have at least one female mating feature and legs of a surgical clip have corresponding male mating features. FIG. 25A shows one embodiment of first and second jaws 1962, 1964 of a surgical clip applier 1960. As shown in FIG. 25A, the first and second jaws 1962, 1964 have respective female mating features in the form of recesses 1972a, 1972b configured to mate with corresponding male mating features in the form of protrusions 1959a, 1959b of first and second legs 1957a, 1957b of a surgical clip 1957. In this example, the recesses 1972a, 1972b and the protrusions 1959a, 1959b have generally rectangular cross-sections. FIG. 25B shows one embodiment of first and second jaws 1962', 1964' of a surgical clip applier 1960'. As shown in FIG. 25A, the first and second jaws 1962', 1964' have respective female mating features in the form of recesses 1972a', 1972b' configured to mate with corresponding male mating features in the form of protrusions 1959a', 1959b' of first and second legs 1957a', 1957b' of a surgical clip 1957'. In this example, the recesses 1972a', 1972b' and the protrusions 1959a', 1959b' have generally semi-circular cross-sections. It should be appreciated that the female mating features of the jaws and the corresponding male mating features in the clip can have various configurations.

In some embodiments, jaws of a surgical clip applier have first and second female mating features on upper and lower rails and legs of a surgical clip have corresponding male mating features formed on surfaces facing the jaw's upper and lower rails. FIG. 26 shows one embodiment of a jaw 2212 of a surgical clip applier 2200. As shown, the jaw 2212 has first and second female mating features 2202a, 2202b in the form of longitudinal recesses formed on upper and lower rails 2201a, 2201b thereof. A leg of a surgical clip 2207 has corresponding first and second male mating features 2209a, 2209b in the form of longitudinal protrusions facing the jaw's female mating features 2202a, 2202b when the clip 2207 is advanced between the jaw 2212 and the opposed jaw (not shown) of the clip applier 2200. It should be appreciated that the opposed leg of the clip 2207, which is not shown in FIG. 26, has similar male mating features. In this example, the longitudinal recesses of the jaw have a generally triangular lateral cross-section, and the clip's longitudinal protrusions 2202a, 2202b also have a generally triangular lateral cross-section.

FIG. 27 shows one embodiment of first and second jaws 2312, 2314 of a surgical clip applier 2300 configured to mate with a surgical clip 2307. In this example, first and second legs 2307a, 2307b of the clip 2307 have respective small protrusions. Thus, the first leg 2307a has first and second longitudinal protrusions 2309a, 2309b on the opposed surfaces facing upper and lower rails of the first jaw 2312, and the second leg 2307b has third and fourth longitudinal protrusions 2309c, 2309d on the opposed surfaces facing upper and lower rails of the second jaw 2314. The protrusions 2309a, 2309b, 2309c, 2309d are small such that, while they facilitate engagement of the clip 2307 with the jaws during clip formation, they do not interfere with release of the formed clip from the jaws. The protrusions 2309a, 2309b, 2309c, 2309d are shown in FIG. 27 to be generally semi-circular, though they can have any other shapes, including different shapes.

FIG. 28 shows one embodiment of first and second jaws 2412, 2414 of a surgical clip applier 2400 configured to mate with a surgical clip 2407. In this example, first and second legs 2407a, 2407b of the clip 2407 have respective longitudinal recesses formed in opposed upper and lower surfaces thereof and configured to mate with corresponding longitudinal protrusions formed on upper and lower rails of the jaws. As shown, the first clip leg 2407a has first and second recesses 2409a, 2409b configured to mate with corresponding first and second longitudinal protrusions 2402a, 2402b on the upper and lower rails of the first jaw 2412. Similarly, the second clip leg 2407b has third and fourth recesses 2409c, 2409d configured to mate with corresponding third and fourth longitudinal protrusions 2402c, 2402d on the upper and lower rails of the second jaw 2414. In this example, the longitudinal recesses 2409a, 2409b, 2409c, 2409d of the clip have a generally triangular lateral cross-section, and the jaw's longitudinal protrusions 2402a, 2402b, 2402c, 2402d also have a generally triangular lateral cross-section.

In some embodiments, as mentioned above, jaws of a surgical clip applier can be at least partially flexible and bendable such that the jaws can be partially, reversibly deformed when a surgical clip is advanced therebetween. Additionally or alternatively, in some embodiments, a surgical clip can be bendable such that it is deformed when advanced between the jaws, for improved retention by the jaws. The jaws and/or the clip can be tapered not only in an axial or longitudinal directions, but only in a transverse direction, to provide biasing forces without a need for additional biasing elements (e.g., springs).

FIG. 29A shows one embodiment of first and second jaws 2512, 2514 of a surgical clip applier 2500 configured to engage with a surgical clip 2507 that is at least partially bendable. Thus, as shown in FIG. 29A, when the clip 2507 is advanced between the jaws 2512, 2514, first and second legs 2507a, 2507b of the clip are deformed, such that, in this example, bent outward with respect to sidewalls 2510a, 2510b of the jaws 2512, 2514. In this embodiment, upper and lower rails of the jaws are angled or tapered inward and towards one another. Thus, for example, upper and lower rails 2511a, 2511b of the first jaw 2512 are tapered inward and towards one another. In this example, as shown, each of the rails is tapered in the transverse direction such that its width increases in a direction away from a jaw's sidewall. Thus, the upper rail 2511a of the jaw 2512 tapers such that its width increases from its portion adjacent to the sidewall 2510a towards the rail's edge 2513. Other rails of the jaws of the surgical clip applier 2500 are configured similarly. Such tapering of the jaws in the transverse direction facilitates engagement of the clip by the jaws, without a need for an additional biasing element. The clip 2507 can be press-fit into between the jaws (and between the rails of each of the jaws), to be releasably retained between the jaws. When the clip 2507 is formed, its configuration is changed such that its legs are no longer bent as shown in FIG. 29A.

FIG. 29B illustrates an embodiment of first and second jaws 2532, 2534 of a surgical clip applier 2520, where the jaws are reversibly deformable and have tapered upper and lower rails. In this embodiment, the first and second jaws 2532, 2534 are configured such that their upper and lower rails are angled inward and towards one another, as shown FIG. 29B. It should be appreciated, however, that in FIG. 29B, the jaws 2532, 2534 are schematically shown as angled more than they are angled in an actual surgical clip applier such as the clip applier 2520, for illustrated purposes only. Also, it should be noted that the jaw's rails can be tapered such that their width changes in the transverse direction and/or such that the entire rail is angled in the transverse direction, as shown in FIG. 29B. The first and second jaws 2532, 2534 are configured such that their upper and lower rails are biased towards the clip 2527. Thus, in this example, the jaws 2532, 2534 have an approximately dovetail shape (which is exaggerated in FIG. 29B, as mentioned above), and a center of gravity of each jaw is below an edge of the jaw, as shown by a reference "C" for the second jaw 2534. When a surgical clip 2527 is advanced between the jaws 2532, 2534, clip's first and second legs 2527a, 2527b are advanced into between upper and lower rails of the respective jaw, and force the upper and lower rails slightly apart to allow to be retained by the jaws. Thus, the first leg 2527a is forced between upper and lower rails 2521a, 2521b of the first jaw 2532, as shown in FIG. 29B, and the second legs 2527b is similarly engaged by the second jaw 2534. When the clip is formed, the jaws release it and revert to their original configuration.

In embodiments in which jaws of a surgical clip applier are configured as shown in FIG. 29B (e.g., upper and lower rails of each jaw are angled inward and toward one another), the jaws retain a surgical clip even in some undesirable circumstances. For example, if the clip is (unintentionally) rotated, the jaws will still retain it properly and release the clip once it is formed. FIG. 29C shows an example of a scenario when a clip is rotated, and one leg 2527a' of such clip (schematically shown rotated) is shown engaged by a jaw 2532'.

Jaws of a surgical clip applier can be in various taper relationships with a surgical clip. FIGS. 30A to 30D illustrate examples of surgical clip appliers in various taper relationships with surgical clips. It should be noted that FIGS. 30A to 30D show the clip appliers and the clips during an initial stage of a clip formation, when the clip has just been advanced between the jaws and the jaws retain the clip while the jaws are still open. Also, in the examples shown in FIGS. 30A-30D, the jaws and/or the clip (or a portion thereof, such as clip's legs) can be at least partially and reversibly deformable.

FIG. 30A shows one embodiment of first and second jaws 2612, 2614 of a surgical clip applier 2600, where the jaws 2612, 2614 are substantially parallel to one another. As also shown in FIG. 30A, a surgical clip 2607, shown disposed between the jaws 2612, 2614 has its legs configured such that they are disposed at an obtuse angle $\Theta c1$ with respect to one another.

FIG. 30B shows another embodiment of first and second jaws 2612', 2614' of a surgical clip applier 2600', where the jaws 2612', 2614' are disposed at an obtuse angle $\Theta j1$ with respect to one another. As also shown in FIG. 30B, a surgical clip 2607', shown disposed between the jaws 2612', 2614", has its legs configured such that they are disposed at an obtuse angle $\Theta c2$ with respect to one another, where angle $\Theta c2$ is greater than angle $\Theta j1$ between the jaws 2612', 2614'.

FIG. 30C shows another embodiment of first and second jaws 2612", 2614" of a surgical clip applier 2600", where the jaws 2612", 2614" are disposed at an acute angle $\Theta j2$ with respect to one another. FIG. 30B also shows a surgical clip 2607", shown disposed between the jaws 2612", 2614", which has its legs configured such that they are disposed substantially parallel to one another.

FIG. 30D shows another embodiment of first and second jaws 2812, 2814 of a surgical clip applier 2800, where the first and second jaws 2812, 2814 are proximally tapered, and where a surgical clip 2807 is shown disposed between the jaws, the clip having first and second legs that are also proximally tapered.

Various clip retention members and other features that facilitate clip retention and alignment can be formed on at least one jaw of a surgical clip applier having any suitable configuration, such as surgical clip applier 100 (FIGS. 1 to 4B), or any other clip applier. The various clip retaining features disclosed herein can have a variety of other configurations, as disclosed in U.S. application Ser. No. 15/674, 121, filed on even date herewith and entitled "Jaw For Clip Applier," which is hereby incorporated by reference in its entirety. Regardless of the specific configuration of the clip applier, the clip retention members maintain the clip in alignment with the jaws and thus help ensure proper formation of the clip.

Figure 31A:
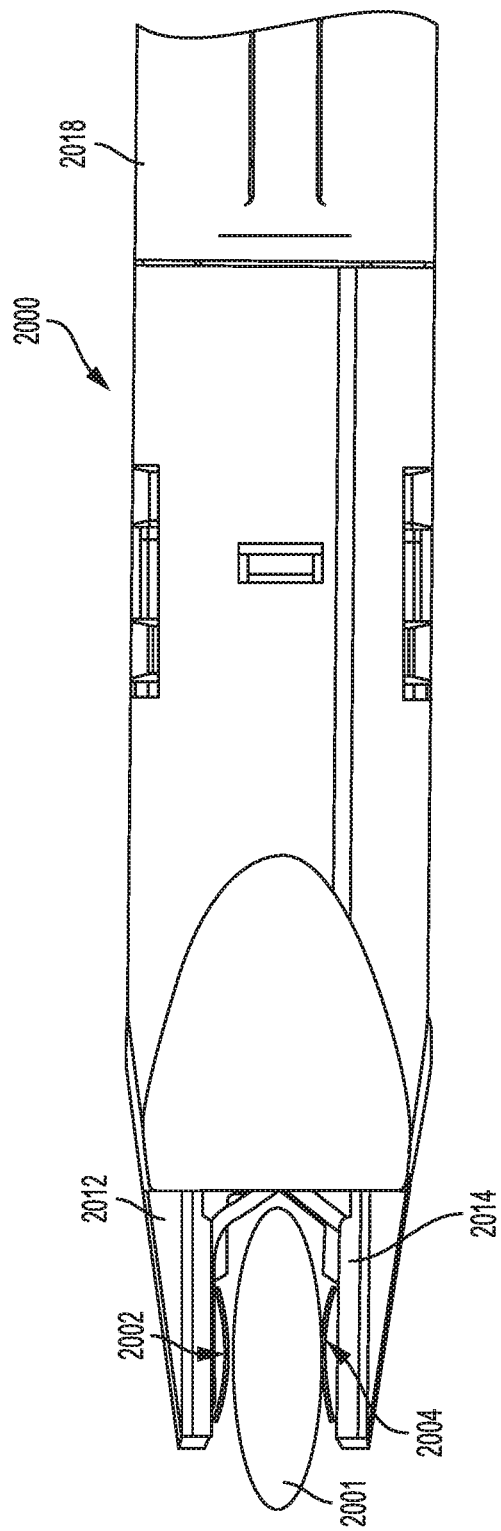
FIG. 31A is a side perspective view of a distal portion of a surgical clip applier, showing jaws of the surgical clip applier positioned around tissue and in an open position during a surgical procedure.
Figure 31B:
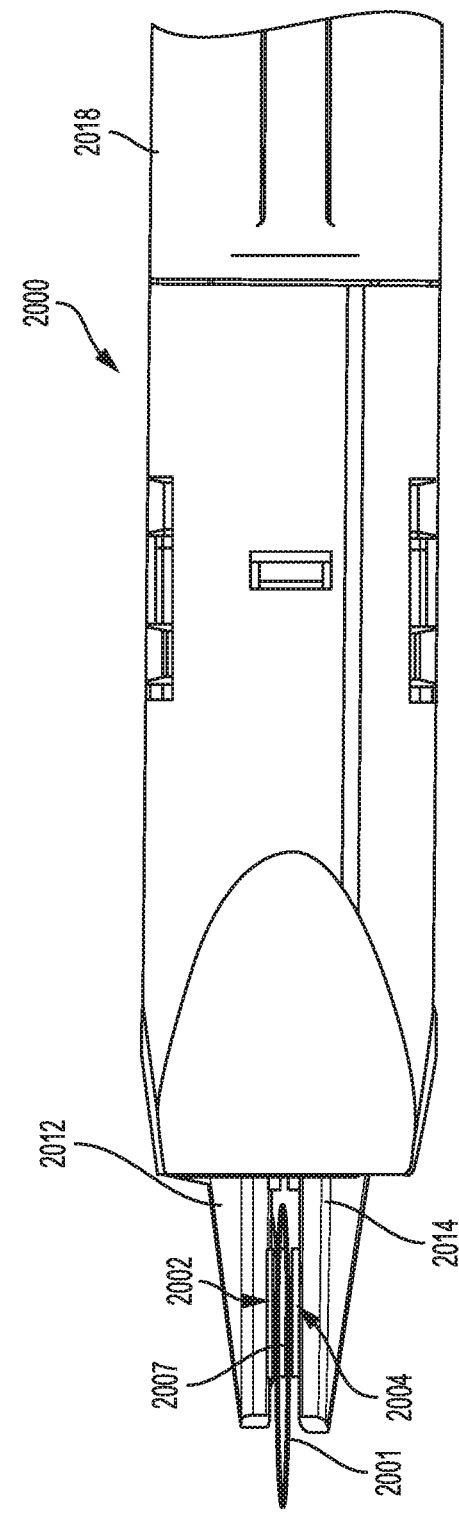
FIG. 31B is a side perspective view of the distal portion of the surgical clip applier of FIG. 31A, showing the jaws of the surgical clip applier in the closed position and a clip formed by the jaws.

FIGS. 31A and 31B illustrate one embodiment of a method for applying a surgical clip to tissue using a surgical clip applier 2000 having first and second jaws 2012, 2014. The surgical clip applier 2000 can be similar, for example, to surgical clip applier 100 (FIGS. 1 to 4B), or it can have any other configuration. Regardless of its specific configuration, the surgical clip applier 2000 can be used to apply a surgical clip to tissue, such as a vessel, duct, shunt, etc., at a surgical site during a surgical procedure. The surgical clip can be applied in a partially or fully closed configuration.

In laparoscopic and endoscopic surgery, a small incision is made in the patient's body to provide access to a surgical site. A cannula or access port can be used to define a working channel extending from the skin incision to the surgical site. It may be required to cease blood flow through the vessels or other ducts during a surgical procedure, and some procedures may thus require the use of a shunt. A surgical clip can thus be used to crimp the vessel or to secure the shunt to the vessel.

Accordingly, a surgical clip applier, such as clip applier 2000, can be introduced through the cannula or otherwise introduced into the surgical site. The first and second jaws 2012, 2014 can be manipulated to position tissue 2001 (e.g., vessel, shunt, or other type of tissue) between the first and second jaws 2012, 2014, as shown in FIG. 31A. Each of the first and second jaws 2012, 2014 can have a respective clip track formed therein that is defined in an inward facing surface of the jaw. The clip track can be, for example, a clip guide channel, such as clip guide channel 206 (FIG. 5A), clip guide channel 306 (FIG. 6), or a clip track having any other configuration. In some embodiments, as discussed above in connection with FIGS. 16 and 17, the clip track can be a separate element coupled to the jaw.

The clip tracks of the first and second jaws 2012, 2014 can have disposed therein resilient clip retention members 2002, 2004, respectively, which are shown in a first, uncompressed configuration in FIG. 31A. The clip retention members 2002, 2004 can be any of the clip retention members described herein. The clip retention members 2002, 2004 can be formed on one or both of an upper surface, lower surface, and sidewall of the clip guide channel. The clip retention members can be leaf springs, other deformable elements (e.g., elastically deformable elements), or any other types of elements. In some embodiments, at least one of the jaws 2012, 2014 can have at least one deflectable tab in the clip track that can prevent proximal movement of the clip within the clip track. In some embodiments, at least one of the jaws 2012, 2014 can have features configured to mate with corresponding features of a clip, as shown, e.g., in FIGS. 23A to 30D. Any other features can be formed on the jaw(s) and the clip to facilitate clip retention by the jaws and maintain alignment of the clip with respect to the jaws.

After tissue 2001 is positioned between the first and second jaws 2012, 2014 as shown in FIG. 31A, the clip applier 2000 can be actuated (e.g., using a trigger, such as trigger 106 of clip applier 100 of FIG. 1) to move the first and second jaws 2012, 2014 from an open position to a closed position to deform a clip 2007 positioned within the clip tracks formed in the first and second jaws 2012, 2014 and thereby engage the tissue 2001 between legs of the clip 2007. The clip 2007, schematically shown in a deformed configuration in FIG. 31B, has been advanced distally and into the jaws 2012, 2014 by a clip advancing assembly extending through an elongate shaft 2018 of the clip applier 2000. The clip retention members 2002, 2004 of the first and second jaws 2012, 2014, which are shown in FIG. 31B in a second, compressed configuration, each apply a biasing force to the clip 2007 to maintain the clip 2007 in alignment with the jaws 2012, 2014 as the jaws 2012, 2014 are moved from the open position to the closed position. The trigger can then be released to release the closed clip 2007 (which can be partially or fully closed), and the procedure can be repeated if necessary to apply additional clips that can be disposed in the elongate shaft 2018.

In some cases, after multiple uses of a surgical clip applier having at least one clip retention member on at least one of jaws thereof, the clip retention strength of the clip retention member and/or a portion of the jaw interacting with the clip can decline. This can occur due to degradation of the material over time due to fatigue, or damage incurred by clips, staples, or other hard structures (e.g., by another surgical tool). Accordingly, in some embodiments, techniques are provided that allow "healing" of the clip retention member such that its clip retention strength is restored. For example, at least a portion of a jaw of a surgical clip applier, or a clip retention member, can be formed from a poly(urea-urethane) (PUU) material that has self-healing properties and is thus tolerant to mechanical damage. The PUU material, or any other suitable polymeric self-healing material, has the ability to automatically repair damage to itself without any human intervention. The self-healing materials can fully or partially restore their physical and mechanical properties, which can be done using an external stimulus (e.g., a catalyst), or a damage can be healed spontaneously. In this way, when the clip retention member or any portion of the jaw serving to retain a clip is formed from such a self-healing material, degradation of device performance over time is reduced. In addition, PUU material is a biocompatible material and is therefore suitable for surgical applications.

FIGS. 32 to 34 illustrate one embodiment of first and second jaws 2112, 2114 of a surgical clip applier 2100 having respective first and second clip retention members 2102, 2104. In this example, each of the clip retention members 2102, 2104 is in the form of a clip track coupled to the respective jaw. A clip track 2106a of the first clip retention member 2112 has an upper wall 2108u, a lower wall 2108l, and a sidewall 2110 extending between the upper and lower walls 2108u, 2108l. The second clip retention member 2114 is a similar clip track 2106a. It should be appreciated that the clip retention members 2102, 2104 are shown in FIG. 32 by way of example only, as they can have any suitable shapes and sizes. For example, any of the clip retention members described herein can be used additionally or alternatively. The clip retention members 2102, 2104 can be separate members made from a plastic elastomer or other resilient material, and they can be coupled to the jaws 2112, 2114 in a suitable manner.

In this embodiment, at least a portion of each of the clip retention members 2102, 2104 includes a self-healing material such as PUU or other self-healing material. For example, the clip retention members 2102, 2104 can be coated with such material such that at least a portion of each clip retention member's surface facing the opposed jaw is formed from the self-healing material. As another variation, the clip retention members 2102, 2104 can be at least partially formed from the self-healing material. Also, in embodiments in which portions of the clip applier's jaws (e.g., inward facing surfaces of the jaws) serve as clip retention features, those portions of the jaws can be formed from the self-healing material, such as, for example, PUU.

FIG. 33 shows an example of how a self-healing material used to form the jaws can alleviate any damage to the jaws when a clip is improperly formed. In this example, after a first clip 2107 is formed around tissue, a second clip 2109 is unintentionally applied over the already formed first clip 2107 (rather than onto the tissue). As shown, the jaws 2112, 2114 are positioned over a tissue 2101 with a previously applied clip 2107. The clip applier 2100 is then activated such that the jaws 2112, 2114 are clamped over the tissue 2101 and the clip 2107, so as to form clip 2109 disposed in the clip tracks 2106a, 2106b of the jaws 2112, 2114. During firing of clip 2109 over tissue 2101 and clip 2107, clip 2109 is pushed against the surfaces of the clip retention members 2102, 2104 applying a biasing force to the clip 2109. Thus, damage to the clip retention members 2102, 2104 can occur, for example, in the form of damages 2113, 2115, 2117 to surfaces of the retention members 2102, 2104, as schematically shown in FIG. 33. The damaged areas 2113, 2115, 2117 can be scratched, cracked, fractured, chipped, dented, or otherwise affected by the second clip 2109 being formed over the formed clip 2107 such that structural integrity and therefore performance of the clip retention members is compromised.

In the illustrated embodiment, because the clip retention members 2102, 2104 are coated with or at least partially made from a PUU or other self-healing material, the damages 2113, 2115, 2117 to the retention members 2102, 2104 can self-heal such that the damaged material returns at least in part to its original (pre-damaged) state. FIG. 34 illustrates that the damaged areas 2113, 2115, 2117 (shown in FIG. 33) are restored and thus labeled as locations 2113', 2115', 2117' in FIG. 34. In this way, decrease in the clip retention strength of the clip retention members is prevented or eliminated. It should be appreciated that any of the clip retention members described herein, or any other clip retention members, can be at least partially made from or can include PUU or other self-healing material. In this way, damage that may occur to the clip retention members during use, can be repaired.

A person skilled in the art will appreciate that the devices, systems, and methods disclosed herein have application in conventional minimally-invasive and open surgical instrumentation as well application in robotic-assisted surgery. In some embodiments, the devices, systems, and methods described herein are provided for open surgical procedures, and in other embodiments, the devices, systems, and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods, systems, and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip applier, comprising:
   an elongate shaft having first and second jaws on a distal end thereof that are movable between open and closed positions for engaging tissue therebetween; and
   a clip advancing assembly extending through the elongate shaft and configured to advance a plurality of clips through the elongate shaft and to advance a distal-most clip of the plurality of clips into the first and second jaws;
   wherein the first and second jaws have opposed inward facing surfaces, each inward facing surface having a clip guide channel formed there along for receiving and guiding legs of the distal-most clip into the first and second jaws, wherein the clip guide channel on at least one of the first and second jaws includes at least one deflectable clip retention member disposed therein and configured to apply a biasing force to at least one leg of the distal-most clip when the distal-most clip is disposed within the first and second jaws to thereby retain the distal-most clip within the first and second jaws; and
   wherein the biasing force is applied in a direction substantially perpendicular to a plane extending through the first and second jaws.

2. The surgical clip applier of claim 1, wherein the at least one deflectable clip retention member extends along a longitudinal length of at least one of the first and second jaws and the biasing force applied by the at least one deflectable clip retention member varies along the longitudinal length.

3. The surgical clip applier of claim 1, wherein the at least one deflectable clip retention member is elastically deformable.

4. The surgical clip applier of claim 1, wherein the at least one deflectable clip retention member comprises a leaf spring.

5. The surgical clip applier of claim 1, wherein the clip guide channel includes an upper surface, a lower surface, and a sidewall extending between the upper and lower surfaces, and wherein the at least one deflectable clip retention member is disposed on the sidewall and biases one leg of the distal-most clip toward the opposed jaw.

6. The surgical clip applier of claim 1, wherein the clip guide channel includes an upper surface, a lower surface, and a sidewall extending between the upper and lower surfaces, and wherein the at least one deflectable clip retention member comprises a first deflectable clip retention member disposed on the upper surface and a second deflectable clip retention member disposed on the lower surface such that the first and second deflectable clip retention members engage one leg of the distal-most clip when disposed therebetween.

7. The surgical clip applier of claim 1, wherein the clip guide channel further includes at least one deflectable tab configured to engage a proximal surface of the distal-most clip after the distal-most clip moves distally past the at least one deflectable tab.

8. The surgical clip applier of claim 1, wherein at least a portion of the at least one deflectable clip retention member comprises a self-healing material.

9. A surgical clip applier, comprising:
   an elongate shaft and first and second jaws on a distal end thereof that are movable between open and closed positions for engaging tissue therebetween, the first and second jaws having inward facing surfaces defining a clip track for receiving and guiding a distal-most clip of a plurality of clips into the jaws, and at least one compressible clip retention member disposed within the clip track in one of the first and second jaws; and
   a clip advancing assembly extending through the elongate shaft and configured to distally advance the plurality of clips through the elongate shaft and to advance the distal-most clip into the clip track in the first and second jaws, the at least one clip retention member being configured to move from a first, uncompressed configuration to a second, compressed configuration when the distal-most clip is advanced into the clip track;
   wherein the at least one clip retention member comprises a first retention member disposed on an upper wall of the clip track and a second retention member disposed on a lower wall of the clip track such that the first and second retention members are configured to engage one leg of the distal-most clip when disposed therebetween.

10. The surgical clip applier of claim 9, wherein a distal portion of at least one of the first retention member or the second retention member is more flexible than a corresponding proximal portion thereof.

11. The surgical clip applier of claim 9, wherein at least one of the first retention member or the second retention member comprises a leaf spring extending longitudinally along at least one of the first and second jaws.

12. The surgical clip applier of claim 9, wherein the clip track further includes at least one deflectable tab configured to engage a proximal surface of the distal-most clip after the distal-most clip moves distally past the at least one deflectable tab.

13. The surgical clip applier of claim 9, wherein a portion of at least one of the first retention member or the second retention member comprises a self-healing material comprising poly(urea-urethane).

14. A surgical clip applier, comprising:
an elongate shaft and first and second jaws on a distal end thereof that are movable between open and closed positions for engaging tissue therebetween, the first and second jaws having inward facing surfaces defining a clip track for receiving and guiding a distal-most clip of a plurality of clips into the jaws, and at least one compressible clip retention member disposed within the clip track in one of the first and second jaws, the at least one clip retention member extending from a first end to a second end; and
a clip advancing assembly extending through the elongate shaft and configured to distally advance the plurality of clips through the elongate shaft and to advance the distal-most clip into the clip track in the first and second jaws, the at least one clip retention member being configured to move from a first, uncompressed configuration to a second, compressed configuration when the distal-most clip is advanced into the clip track;
wherein the first and second ends are in contact with the clip track when the at least one clip retention member is at least in the first, uncompressed configuration.

15. The surgical clip applier of claim 14, wherein the first and second ends are in contact with the clip track when the at least one clip retention member is in the second, compressed configuration.

16. The surgical clip applier of claim 14, wherein the at least one clip retention member is disposed on a sidewall of the clip track, the sidewall extending between upper and lower walls of the clip track.

17. The surgical clip applier of claim 14, wherein the at least one clip retention member is disposed on at least one of an upper wall, a lower wall, or a sidewall of the clip track, the sidewall extending between the upper and lower walls.

18. The surgical clip applier of claim 14, wherein the clip track further includes at least one deflectable tab configured to engage a proximal surface of the distal-most clip after the distal-most clip moves distally past the at least one deflectable tab.

19. The surgical clip applier of claim 14, wherein the at least one clip retention member comprises a leaf spring.

* * * * *